US006930088B2

(12) United States Patent
Hornik et al.

(10) Patent No.: US 6,930,088 B2
(45) Date of Patent: Aug. 16, 2005

(54) CONFORMATIONALLY CONSTRAINED BACKBONE CYCLIZED SOMATOSTATIN ANALOGS

(75) Inventors: Vered Hornik, Rehovot (IL); Michel M. Afargan, Raanana (IL); Gary Gellerman, Rishon LeZion (IL)

(73) Assignee: Peptor Ltd., Rehovot (IL)

( * ) Notice: Subject to any disclaimer, the term of this patent is extended or adjusted under 35 U.S.C. 154(b) by 772 days.

(21) Appl. No.: 09/734,583

(22) Filed: Dec. 13, 2000

(65) Prior Publication Data

US 2002/0052315 A1 May 2, 2002

Related U.S. Application Data

(63) Continuation of application No. PCT/IL99/00329, filed on Jun. 15, 1999, which is a continuation-in-part of application No. 09/203,389, filed on Dec. 2, 1998, now Pat. No. 6,355,613, which is a continuation-in-part of application No. 09/100,360, filed on Jun. 19, 1998, now Pat. No. 6,051,554.

(51) Int. Cl.$^7$ ............................................. A61K 38/00
(52) U.S. Cl. .............................. 514/9; 514/11; 530/311
(58) Field of Search ........................ 514/9, 11; 530/311

(56) References Cited

U.S. PATENT DOCUMENTS

| | | | | |
|---|---|---|---|---|
| 3,988,304 | A | 10/1976 | Garsky | 260/78 A |
| 4,011,182 | A | 3/1977 | Sarantakis | 260/8 |
| 4,054,558 | A | 10/1977 | Garsky | 260/112.5 S |
| 4,187,217 | A | 2/1980 | Chipens et al. | 260/112.5 R |
| 4,191,754 | A | 3/1980 | Veber et al. | 424/177 |
| 4,235,886 | A | 11/1980 | Freidinger et al. | 424/177 |
| 4,310,518 | A | 1/1982 | Freidinger et al. | 424/177 |
| 4,395,403 | A * | 7/1983 | Bauer et al. | 424/177 |
| 5,364,851 | A | 11/1994 | Joran | 530/345 |
| 5,371,070 | A | 12/1994 | Koerber et al. | 514/9 |
| 5,770,687 | A * | 6/1998 | Hornik et al. | 530/311 |
| 5,811,392 | A | 9/1998 | Gilon et al. | 514/11 |
| 5,874,529 | A | 2/1999 | Gilon et al. | 530/317 |
| 6,051,554 | A * | 4/2000 | Hornik et al. | 514/11 |
| 6,355,613 | B1 * | 3/2002 | Hornik et al. | 514/9 |

FOREIGN PATENT DOCUMENTS

| | | |
|---|---|---|
| EP | 0 334 244 A2 | 9/1989 |
| EP | 0 336 779 A2 | 10/1989 |
| EP | 0 370 453 B1 | 5/1990 |
| EP | 0 336 779 A3 | 8/1991 |
| EP | 0 564 739 A2 | 10/1993 |
| EP | 0 564 739 A3 | 4/1995 |
| FR | 2304352 | 10/1976 |
| FR | 2411828 | 7/1979 |
| WO | WO 89/01781 | 3/1989 |
| WO | WO 92/00091 | 1/1992 |
| WO | WO 92/22566 | 12/1992 |
| WO | WO 93/01206 | 1/1993 |
| WO | WO 94/11393 | 5/1994 |

OTHER PUBLICATIONS

Arad et al. (including Afargan Gellerman, Hornik). Backbone–cyclic peptides in peptide drug discovery. Book of Abstracts, 211$^{th}$ ACS National Meeting, New Orleans, LA, Mar. 24–28 (1996), I & EC–012. American Chemical Society: Washington, D.C.*

Kaljuste, et al. A new general solid–phase method for the synthesis of backbone–to–backbone cyclized peptides. Int J Pept Protein Res. May 1994;43(5):505–511.*

Bell et al., 1993, "Molecular biology of somatostatin receptors," TINS, vol. 16, No. 1, 34–38.

Brazeau et al, 1973, "Hypothalamic Polypeptide That Inhibits the Secretion of Immunoreative Pituitary Growth Hormone", SCIENCE, vol. 179, pp. 77–79.

Buscail et al., 1995, "Inhibition of cell proliferation by the somatostatin analogue RC–160 is mediated by somatostatin receptor subtypes SSTR2 and SSTR5 through different mechanisms," Proc. Natl. Acad. Sci. USA 92: 1580–1584.

Byk et al., 1992, "Building units for N–backbone cyclic peptides. I. Synthesis of protected N–(ω–aminoalkylene)amino acids and their incorporation into dipeptide units", J. Org. Chem. 57:5687–5692.

Charpentier et al., 1989, "Synthesis and binding affinities of cyclic and related linear analogues of CCK$_8$ selective for central receptors," J. Med. Chem., pp. 1184–1190.

Giannis et al., 1993, "Peptidomimetics for receptor ligands—discovery, development, and medical perspectives," Angew. Chem. Int. Ed. Engl. 32: 1244–1267.

Gilon et al., 1991, "Backbone Cyclization: A New Method for Conferring Conformational Constraint on Peptides", *Biopolymers* 31:745–750.

Gilon et al., 1992, "SAR studies of cycloseptide: effects of cyclization and charge at position 6," Chem. Biol. Proc. Am. Pept. Symp 1th. pp. 476–477.

Greiner et al., "Synthesis of New Backbone–Cyclized Bradykinin Analogs", *Proc. Eur. Pept. Symp.*, 23rd, Meeting Date 1994, 289–290.

Hruby et al., 1990, "Emerging approaches in the molecular design of receptor–selective peptide ligands: conformational, topographical and dynamic considerations," Biochem. J. 298: 249–262.

Krstenansky et al., 1994, "Cyclic Hexapeptide anatagonists of the bradykinin B$_2$ receptor: Receptor binding and solution backbone conformation", *Letters in Peptide Science* 1:229–234.

(Continued)

Primary Examiner—Christopher R. Tate
Assistant Examiner—Maury Audet
(74) Attorney, Agent, or Firm—Winston & Strawn LLP

(57) ABSTRACT

Novel peptides which are conformationally constrained backbone cyclized somatostatin analogs, having somatostatin receptor subtype selectivity are disclosed. These patterns or receptor subtype selectivity provide compounds having improved therapeutic utility. Methods for synthesizing the somatostatin analogs and for screening of the somatostatin analogs are also disclosed. Furthermore, pharmaceutical compositions comprising somatostatin analogs, and methods of using such compositions are disclosed.

18 Claims, 5 Drawing Sheets

OTHER PUBLICATIONS

Lamberts, 1988, "The role of Somastatin in the regulation of anterior pituitary hormone secretion and the use of its analogs in the treatment of human pituitary tumors," Endocrine Reviews vol. 9, No. 4, pp. 417–436.

Lamberts et al., 1990,"Somastatin–receptor imaging in the localization of endocrine tumors," New England J. Med. 323:1246–1249.

Lymangrover et al., 1993, "Varying the duration of A23187 administration alters its effect on adrenal steroidogenesis," Life sciences 34:371–377.

Mosberg et al., 1983, "Bis–penicillamine enkephalins possess highly improved specificity toward δ opioid receptors," Biochemistry 80:5871–5874.

Plotsky et al., 1985, "Patterns of growth hormone–releasing factor and somatostatin secretion into the hypophysial–portal circulation of the rat," Science 230:461–463.

Raynor et al., 1993, "Cloned somatostatin receptors: identification of subtype–selective peptides and demonstration of high affinity binding of linear peptides," Mol. pharmacol. 43:838–844.

Reisine et al., 1995, "Molecular biology of somatostatin receptors," Endocrine reviews 16, 427–442.

Reubi et al., 1995, "Multiple actions of somatostatin in neoplastic disease," TIPS 16: 110–115.

Rizo et al., 1992, "Constrained peptides: Models of bioactive peptides and protein substructures," Annu. Rev. Biochem. 61:387–418.

Rodriguez et al. 1990, "Synthesis of cyclic analogues of cholecystokinin highly selective for central receptors," Int. J. Peptide Protein Res. 35:441–451.

Steranka et al., 1988, "Bradykinin as a pain mediator: receptors are localized to sensory neurons, and antagonists have analgesic actions," Proc. Natl. Acad. Sci. USA 85:3245–3249.

Verber et al., 1984, "A super active cyclic hexapeptide analog of somatostatin," Life sciences 34:1371–1378.

Verber et al., 1985, "The design of metabolically–stable peptide analogs," TINS, pp. 392–396.

Zuckerman, 1993, "The chemical synthesis of peptidomimetic libraries," Current Opinion in Structure Biol., 3: 580–584.

* cited by examiner

A.

B.

*P< 0.05 Dunnett ± S.E

CONFORMATIONALLY CONSTRAINED BACKBONE CYCLIZED SOMATOSTATIN ANALOGS

CROSS REFERENCE TO RELATED APPLICATIONS

This application is a continuation of the U.S. national stage designation of PCT application No. PCT/IL99/00329 filed Jun. 15, 1999, which is a continuation-in-part of application Ser. No. 09/203,389 filed Dec. 2, 1998, now U.S. Pat. No. 6,355,613, which in turn is a continuation-in-part of application Ser. No. 09/100,360 filed Jun. 19, 1998, now U.S. Pat. No. 6,051,554.

FIELD OF THE INVENTION

The present invention relates to conformationally constrained $N^\alpha$ backbone-cyclized somatostatin analogs cyclized via novel linkages, and to pharmaceutical compositions containing same.

BACKGROUND OF THE INVENTION

Somatostatin Analogs

Somatostatin is a cyclic tetradecapeptide found both in the central nervous system and in peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (for review see Lamberts, *Endocrine Rev.*, 9:427, 1988). Additionally, somatostatin and its analogs are potentially useful antiproliferative agents for the treatment of various types of tumors.

Natural somatostatin (also known as Somatotropin Release Inhibiting Factor, SRIF) of the following structure:

H-Ala$^1$-Gly$^2$-Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$-OH   (SEQ ID NO:1)

was first isolated by Guillemin and colleagues (Bruzeau et al. *Science*, 179:78, 1973). It exerts its effect by interacting with a family of receptors. Recently, five receptor subtypes, termed SSTR1 to 5, have been identified and cloned. The precise functional distinction between these receptor subtypes has not yet been fully elucidated.

In its natural form, somatostatin has limited use as a therapeutic agent since it exhibits two undesirable properties: poor bioavailability and short duration of action. For this reason, great efforts have been made during the last two decades to find somatostatin analogs that will have superiority in either potency, biostability, duration of action or selectivity with regard to inhibition of the release of growth hormone, insulin or glucagon.

Structure-activity relation studies, spectroscopic techniques such as circular dichroism and nuclear magnetic resonance, and molecular modeling approaches reveal the following: the conformation of the cyclic part of natural somatostatin is most likely to be an antiparallel β-sheet; Phe$^6$ and Phe$^{11}$ play an important role in stabilizing the pharmacophore conformation through hydrophobic interactions between the two aromatic rings; the four amino acids Phe$^7$-Trp$^9$-Lys$^9$-Thr$^{10}$ which are spread around the β-turn in the antiparallel β-sheet are essential for the pharmacophore; and (D)Trp$^8$ is preferable to (L)Trp$^8$ for the interactions with somatostatin receptor subtypes 2 through 5.

Nevertheless, a hexapeptide somatostatin analog containing these four amino acids anchored by a disulfide bridge:

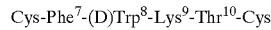

(SEQ ID NO: 2)

is almost inactive both in vitro and in vivo, although it has the advantage of the covalent disulfide bridge which replaces the Phe sup 6-Phe sup. 11 hydrophobic interactions in natural somatostatin.

Four main approaches have been attempted in order to increase the activity of this hexapeptide somatostatin analog. (1) Replacing the disulfide bridge by a cyclization which encourages a cis-amide bond, or by performing a second cyclization to the molecule yielding a bicyclic analog. In both cases the resultant analog has a reduced number of conformational degrees of freedom. (2) Replacing the original residues in the sequence Phe$^7$-(D)Trp$^8$-Lys$^9$-Thr$^{10}$ with other natural or non-natural amino acids, such as replacing Phe$^7$ with Tyr$^7$ and Thr$^{10}$ with Val$^{10}$. (3) Incorporating additional functional groups from natural somatostatin with the intention that these new elements will contribute to the interaction with the receptor. (4) Eliminating one of the four amino acids Phe$^7$-(D)Trp$^8$-Lys$^9$-Thr$^{10}$ with the assumption that such analogs would be more selective.

The somatostatin analog, MK-678:

cyclo(N-Me-Ala$^6$-Tyr$^7$-(D)Trp$^8$-Lys$^9$-Val$^{10}$-Phe)   (SEQ ID NO:3)

is an example of a highly potent somatostatin analog designed using the first three approaches above (Veber, et al., *Life Science*, 34:371, 1984). In this hexapeptide analog, a cis-amide bond is located between N-Me-Ala and Phe$^{11}$, Tyr$^7$ and Val$^{10}$ replace Phe$^7$ and Thr$^{10}$ respectively, and Phe$^{11}$ is incorporated from natural somatostatin.

Another group of somatostatin analogs (U.S. Pat. Nos. 4,310,518 and 4,235,886) includes Octreotide:

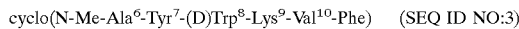

(SEQ ID NO: 4)

the first approved somatostatin analog clinically available and it was developed using the third approach described above. Here, (D)Phe$^5$ and the reduced C-terminal Thr$^{12}$-CH$_2$OH are assumed to occupy some of the conformational space available to the natural Phe$^6$ and Thr$^{12}$, respectively.

The compound TT-232.

(SEQ ID NO: 5)

is closely related to Octreotide and is an example of implementing the fourth approach described above. The lack of Thr$^{10}$ is probably responsible for its high functional selectivity in terms of antitumor activity.

These examples of highly potent somatostatin analogs suggest that the phenylalanines in positions 6 and 11 not only play an important role in stabilizing the pharmacophore conformation but also have a functional role in the interaction with the receptor. It is still an open question whether one phenylalanine (either Phe$^6$ or Phe$^{11}$) is sufficient for the interaction with the receptor or whether both are needed.

It is now known that the somatostatin receptors constitute a family of five different receptor subtypes (Bell and Reisine, *Trends Neurosci.*, 16, 34–38, 1993), which may be distinguished on the basis of their tissue specificity and/or biological activity.

Therapeutic Uses of Somatostatin Analogs

By virtues of their inhibitory pharmacological properties, somatostatin analogs can be used for the treatment of patients with hormone-secreting and hormone-dependent tumors. At the present, symptoms associated with metastatic carcinoid tumors (flushing, diarrhea, valvular heart disease, and abdominal pain) and vasoactive intestinal peptide (VIP) secreting adenomas (watery diarrhea) are treated with Octreotide. Octreotide has also been approved for the treatment of severe gastrointestinal hemorrhages and Acromegaly. In addition, the abundance of high affinity somatostatin receptors in various tumors enables the use of radio-label somatostatin analogs in-vivo for visualization of these tumors (Lamberts et al. *N. Engl. J. Med.*, 334:246 1996). In neuroendocrine tumors, particularly Carcinoids and VIPomas, Oceotide inhibits both the secretion and the effect of the active agent. Thus, in VIPomas characterized by profuse secretory diarrhea, Somatostatin analogs reduce the diarrhea through the inhibition of VIP secretion, and by direct effect on intestinal secretion. However, response to the drug often decreases with time, possibly due to down-regulation of somatostatin receptors on tumor cells or to the generation of receptor negative clone. The absence of consistent antiproliferative effect may be related to the poor affinity of Octeotide to some of the somatostatin receptor subtypes found in these tumors (Lamberts et al. Ibid.).

Native somatostatin and Octreotide reportedly improve secretory diarrhea symptoms, other than those associated with neuroendocrine tumors. Control of secretory diarrhea associated with short bowel syndrome, ileostomy diarrhea, idiopathic secretory diarrhea associated with amyloidosis, and diabetic diarrhea have been reported. Both compounds have also shown some promise in the management of refractory diarrhea related to AIDS, especially in patients without identifiable pathogens. Somatostatin analogs known in the art may not provide sufficient selectivity or receptor subtype selectivity, particularly as anti-neoplastic agents (reubi and Laissue, *TIPS*, 16, 110–115, 1995).

Somatostatin analogs selective to type 2 and 5 receptors which inhibit growth hormone but not insulin release may potentially be used for treatment of Non Insulin Dependent Diabetes Mellitus (NIDDM). Lower potency on glucagon-release inhibition is preferred for reduction of peripheral resistance to insulin and improvement of glycemic-control.

Growth hormone is a direct antagonist of the insulin receptor in the periphery and growth hormone overproduction is associated with insulin peripheral resistance. Elevated IGF, which is the principal biological signal of growth hormone, is associated with diabetic complications such as angiopathy, retinopathy, and nephropathy. Nephropathy is one of the major complications of diabetic angiopathy and one of the leading causes of end stage renal failure and death in diabetic patients. Evidence of the significant involvement of the GH-IGF axis in diabetic and other nephropathies has been provided by several studies (Flyvbjerg A. *Kidney Int.* S12-S19, 1997). It was recently found that increased serum growth hormone levels in the Non-Obese-Diabetic (NOD) mice are similiar to the changes described in humans (Landau et al., *J. Am. Soc. Nephrol.* 8:A2990, 1997). These finding enable the slucidation of the role of the growth hormone-IGF axis in diabetic retinopathy and testing somatostatin analogs for potentially therapeutic effect in these secondary diabetes-associated complications.

Improved Peptide Analogs

It would be desirable to achieve peptide analogs with greater specificity to receptor subtypes therby achieving enhanced clinical selectivity.

As a result of major advances in organic chemistry and in molecular biology, many bioactive peptides can now be prepared in quantities sufficient for pharmacological and clinical utilities. Thus in the last few years new methods have been established for the treatment and therapy of illnesses in which peptides have been implicated. However, the use of peptides as drugs is limited by the following factors: a) their low metabolic stability towards proteolysis in the gastrointestinal tract and in serum; b) their poor absorption after oral ingestion, in particular due to their relatively high molecular mass or the lack of specific transport systems or both; c) their rapid excretion through the liver and kidneys; and d) their undesired side effects in non-target organ systems, since peptide receptors can be widely distributed in an organism.

It would be most beneficial to produce conformationally constrained peptide analogs overcoming the drawbacks of the native peptide molecules, thereby providing improved therapeutic properties.

A novel conceptual approach to the conformational constraint of peptides was introduced by Gilon, et al., (*Biopolymers* 31:745, 1991) who proposed backbone to backbone cyclization of peptides. The theoretical advantages of this strategy include the ability to effect cyclization via the carbons or nitrogens of the peptide backbone without interfering with side chains that may be crucial for interaction with the specific receptor of a given peptide. While the concept was envisaged as being applicable to any linear peptide of interest, in point of fact the limiting factor in the proposed scheme was the availability of suitable building units that must be used to replace the amino acids that are to be linked via bridging groups. The actual reduction to practice of this concept of backbone cyclization was prevented by the inability to devise any practical method of preparing building units of amino acids other than glycine (Gilon et al., *J. Org. Chem.*, 587:5687 1992).

Further disclosures by Gilon and coworkers (WO 95/33765 and WO 97/09344) provided methods for producing building units required in the synthesis of backbone cyclized peptide analogs. Recently, the successful use of these methods to produce backbone cyclized peptide analogs having somatostatin activity was also disclosed (WO 98/04583). All of these methods are incorporated herein in their entirety, by reference.

None of the background art teaches or suggest the somatostatin analogs disclosed herein having improved therapeutic selectivity.

SUMMARY OF THE INVENTION

According to the present invention, novel peptide analogs, which are characterized in that they incorporate novel building units with bridging groups attached to the alpha nitrogens of alpha amino acids, have now been generated. Specifically, these compounds are backbone cyclized somatostatin analogs comprising a peptide sequence of four to twelve amino acids that incorporates at least one building unit, said building unit containing one nitrogen atom of the peptide backbone connected to a bridging group comprising an amide, thioether, thioester or disulfide, wherein the at least one building unit is connected via said bridging group to form a cyclic structure with a moiety selected from the group consisting of a second building unit, the side chain of an amino acid residue of the sequence or the N-terminal amino acid residue. Preferably, the peptide sequence incorporates 4 to 14 amino acids, more preferably 4–12 amino acids, and most preferably 5–9 amino acids.

Heretofore conformationally constrained backbone cyclized somatostatin analogs had selectivity predominantly to receptor subtype 5. These analogs were of limited therapeutic or diagnostic utility.

According to the present invention it is now disclosed that more preferred analogs are hexapeptide analogs with improved selectivity to the SST subtype 3 rather than subtype 5. Most preferred analogs include novel octapeptide analogs of somatostatin which display receptor selectivity to SST subtypes 2 and 5. Additional more preferred somatostatin analogs may advantageously include bicyclic structures containing at least one cyclic structure connecting two building units and a second cyclic structure which is selected from the group consisting of side-chain to side-chain; backbone to backbone and backbone to end. Some of these bicyclic analogs display receptor selectivity to the SST subtype 2.

For certain hexapeptide preferred analogs of the present invention (denoted herein PTR numbers 3123, 3113 and 3171), the amino acid Asn was substituted by the backbone Phe building unit at position 5. The configuration substitution of the native L-Trp at position 8 to D-Trp was made to improve the stability of the analog. The Thr residue at position 10 was substituted by the corresponding backbone Phe building unit. The unique configuration substitution at position 9 from L-Lys to D-Lys as shown in PTRs 3123 and 3171 in comparison to PTR 3113 imparts improved selectivity of binding to the SST receptor subtype SSTR3 rather than SSTR5.

A currently most preferred analog of the present invention is PTR 3173 having improved selectivity of binding to the SST receptor subtype SST-R2 and SST-R5.

For additional most preferred analogs disclosed, the bridge is connected between $N^{\alpha}$-ω-functionalized derivative of an amino acid and the N-terminus of the peptide sequence. For other preferred analogs of the present invention the bridge is connected between a building unit comprising an $N^{\alpha}$-ω-functionalized derivative having a terminal thio group and another such derivative of an amino acid, or to the side chain of a Cys residue, to a mercapto-containing acid or to any other SH containing moiety to form a disulfide bridge.

For preferred analogs further substitutions of amino acids are disclosed. For example substitutions of Phe residues with N-Methyl-Phe residues for increasing the bio-availability of the compound and conjugation of mono- and di-saccharides moieties at the amino terminus for increasing oral bio-availability.

The most preferred backbone cyclized somatostatin analogs of the invention are described in table 1:

TABLE 1

The most preferred analogs.

| PTR | Sequence |
| --- | --- |
| 3171 | Phe*-Phe-Phe-(D)Trp-(D)Lys-Phe(C2)-X |
| 3113 | Phe(C1)-Phe-Phe-(D)Trp-Lys-Phe(N2)-X |
| 3123 | Phe(C1)-Phe-Phe-(D)Trp-(D)Lys-Phe(N2)-X |
| 3209 | Phe(N2)-Tyr-(D)2Nal-Lys-Val-Gly(C2)-Thr-X |
| 3183 | Phe(N2)-Tyr-(D)Trp-Lys-Val-Gly(C2)-2Nal-X |
| 3185 | Phe(N2)-Tyr-(D)Trp-Lys-Val-Val-Gly(C2)-X |
| 3201 | Phe(N2)-Tyr-(D)Trp-Lys-Ser-2Nal-Gly(C2)-X |

TABLE 1-continued

The most preferred analogs.

| PTR | Sequence |
| --- | --- |
| 3203 | Phe(N2)-Phe-(D)Trp-Lys-Thr-2Nal-Gly(C2)-X |
| 3173 | GABA*-Phe-Trp-(D)Trp-Lys-Thr-Phe-Gly(C3)-X |
| 3197 | Cys*-Phe-Trp-(D)Trp-Lys-Thr-Phe-Gly(S2)-X |
| 3205 | Phe(C3)-Cys*-Phe-(D)Trp-Lys-Thr-Cys*-Phe-Phe(N3)-X |
| 3207 | (D)Phe-Cys*-Phe-Trp-(D)Trp-Lys-Thr-Phe-Gly(S2)-X |
| 3229 | Galactose-Dab*-Phe-Trp-(D)Trp-Lys-Thr-Phe-Gly(C3)-X | where X is —NH$_2$ or —OH and the bridging group extends between the two building units or as indicated below:

For PTR 3171 and PTR 3173, the asterisk denotes that the bridging group is connected between the $N^{\alpha}$-ω-functionalized derivative of an amino acid and the N terminus of the peptide. For PTR 3197 and PTR 3207, the asterisk denotes that the bridging group is connected between the $N^{\alpha}$-ω-functionalized derivative of an amino acid and the side chain of the Cys residue. PTR 3205 is a bicyclic compound in which one bridge connects the two building units (Phe-C3 and Phe-N3) and the second is a disulfide bridge formed between the two Cys residues. SSTR indicates the somatostatin receptor subtypes to which each analog is selective.

These backbone cyclized somatostatin peptide analogs are prepared by incorporating at least one $N^{\alpha}$-ω-functionalized derivative of an amino acids into a peptide sequence and subsequently selectively cyclizing the functional group with one of the side chains of the amino acids in the peptide sequence or with another ω-functionalized amino acid derivative. The $N^{\alpha}$-ω-functionalized derivative of amino acids preferably have the following formula:

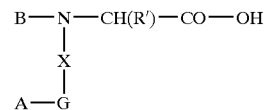

Formula No. 1 wherein X is a spacer group selected from the group consisting of alkylene, substituted alkylene, arylene, cycloalkylene and substituted cycloalkylene; R' is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G.

Preferred building units are the ω-functionalized amino acid derivatives wherein X is alkylene; G is a thiol group, an amine group or a carboxyl group; R' is phenyl, methyl or isobutyl; with the proviso that when G is an amine group, R' is other than H. Further preferred are ω-functionalized amino acid derivatives wherein R' is protected with a specific protecting group.

More preferred are ω-functionalized amino acid derivatives wherein G is an amino group, a carboxyl group, or a thiol group of the following formulae:

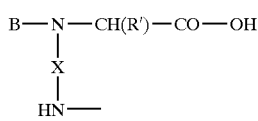

Formula No. 2

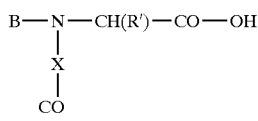

Formula No. 3

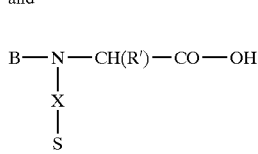

Formula No. 4 wherein X, R' and B are as defined above.

The most striking advantages of these methods are:
1) cyclization of the peptide sequence is achieved without compromising any of the side chains of the peptide thereby decreasing the chances of sacrificing functional groups essential for biological recognition and function.
2) optimization of the peptide conformation is achieved by allowing permutation of the bridge length, direction, and bond type (e.g., amide, disulfide, thioether, thioester, etc.) and position of the bond in the ring.
3) when applied to cyclization of linear peptides of known activity, the bridge can be designed in such a way as to minimize interaction with the active region of the peptide and its cognate receptor. This decreases the chances of the cyclization arm interfering with recognition and function, and also creates a site suitable for attachment of tags such as radioactive tracers, cytotoxic drugs, light capturing substances, or any other desired label.

Backbone cyclized analogs of the present invention may be used as pharmaceutical compositions and in methods for the treatment of disorders including: cancers (including carcinoid syndrome), endocrine disorders (including acromegaly and NIDDM), diabetic-associated complications (including diabetic nephropathy, diabetic angiopathy, and diabetic retinopathy), gastrointestinal disorders, pancreatitis, autoimmune diseases (including Rheumatoid Arthritis and psoriasis), atherosclerosis, restenosis, post-surgical pain, and inflammatory diseases. In assition, somatostatin analogs according to the present invention will be useful in the prevention of atherosclerosis and restenosis by inhibition of growth factors involved in these disorders.

The preferred analogs disclosed in the present invention possess unique features of metabolic stability, selectivity in their in-vivo activities and safety. The most preferred analog disclosed (PTR 3173), offers a drug candidate with a clear therapeutic potential, for the treatment of Carcinoid tumors, Acromegaly, and diabetic-associated complications. This most preferred analog has significant advantages over any other somatostatin analog currently available, in that it is equipotent to available somatostatin analogs in growth hormone inhibition without appreciable effects on insulin or glucagon.

The pharmaceutical compositions comprising pharmacologically active backbone cyclized somatostatin agonists or antagonists and a pharmaceutically acceptable carrier or diluent represent another embodiment of the invention, as do the methods for the treatment of cancers, endocrine disorders, diabetic-associated complications, gastrointestinal disorders, pancreatitis, autoimmune diseases, atherosclerosis, restenosis, and inflammatory diseases. The pharmaceutical compositions according to the present invention advantageously comprise at least one backbone cyclized peptide analog which is selective for one or two somatostatin receptor subtypes. These pharmaceutical compositions may be administered by any suitable route of administration, including topically or systemically. Preferred modes of administration include but are not limited to parenteral routes such as intravenous and intramuscular injections, as well as via nasal or oral ingestion.

Backbone cyclized analogs of the present invention may also be used as pharmaceutical compositions in methods for diagnosing cancer and imaging the existence of tumors or their metastases. The methods for diagnosis of cancer comprise administering to a patient a backbone cyclic analog or analogs labeled with a detectable probe which is selected from the group consisting of a radioactive isotope and a non-radioactive tracer. The methods for the diagnosis or imaging of cancer using such compositions represent another embodiment of the invention.

DETAILED DESCRIPTION OF THE INVENTION

Figure 1:
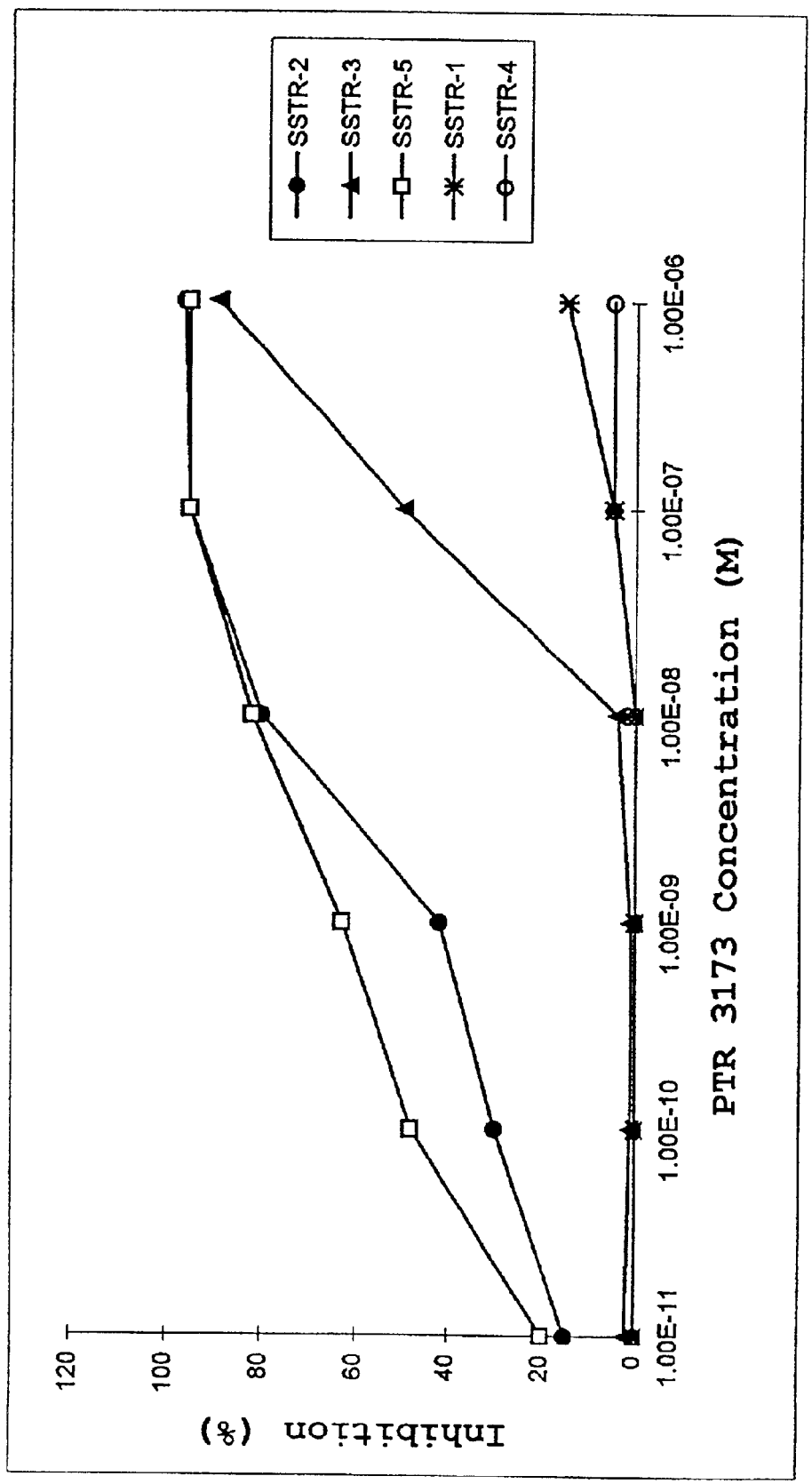
FIG. 1 is a graph showing the percent inhibition of SRIF binding to the 5 human cloned somatostatin receptors by PTR-3173.

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein and in the claims, "alkyl" or "alkylenyl" is intended to include both branched and straight-chain saturated aliphatic hydrocarbon groups having one to ten carbon atoms; "alkenyl" is intended to include hydrocarbon chains of either a straight or branched configuration having two to ten carbon atoms and one or more unsaturated carbon-carbon bonds which may occur in any stable point along the chain, such as ethenyl, propenyl, and the like; and "alkynyl" is intended to include hydrocarbon chains of either a straight or branched configuration having from two to ten carbon atoms and one or more triple carbon-carbon bonds which may occur in any stable point along the chain, such as ethynyl, propynyl, and the like.

As used herein and in the claims, "aryl" is intended to mean any stable 5- to 7-membered monocyclic or bicyclic or 7- to 14-membered bicyclic or tricyclic carbon ring, any of which may be saturated, partially unsaturated or aromatic, for example, phenyl, naphthyl, indanyl, or tetrahydronaphthyl tetralin, etc.

As used herein and in the claims, "alkyl halide" is intended to include both branched and straight-chain saturated aliphatic hydrocarbon groups having the one to ten carbon atoms, wherein 1 to 3 hydrogen atoms have been replaced by a halogen atom such as Cl, F, Br, and I.

As used herein and in the claims, the phrase "therapeutically effective amount" means that amount of novel backbone cyclized peptide analog or composition comprising same to administer to a host to achieve the desired results for the indications described herein, such as but not limited to inflamatory diseases, cancer, endocrine disorders and gastrointestinal disorders.

The term "substituted" as used herein and in the claims, means that any one or more hydrogen atoms on the designated atom is replaced with a selection from the indicated group, provided that the designated atom's normal valency is not exceeded, and that the substitution results in a stable compound.

When any variable (for example R, X, Z, etc.) occurs more than one time in any constituent or in any Formula herein, its definition on each occurrence is independent of its definition at every other occurrence. Also, combinations of substituents and/or variables are permissible only if such combinations result in stable compounds.

As used herein "peptide" indicates a sequence of amino acids linked by peptide bonds. The somatostatin peptide analogs of this invention comprise a sequence of amino acids of 4 to 24 amino acid residues, preferably 6 to 14 residues, each residue being characterized by having an amino and a carboxy terminus.

A "building unit" indicates an $N^\alpha$ derivatized α amino acid of the general Formula No. 5:

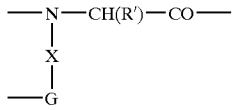

Formula No. 5 wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative.

The methodology for producing the building units is described in international patent applications published as WO 95/33765 and WO 98/04583 and in U.S. Pat. Nos. 5,770,687 and 5,883,293, all of which are expressly incorporated herein by reference thereto as if set forth herein in their entirety. The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and a two carbon methylene spacer, and Phe-N3 designates a modified phenylalanine group with an amino reactive group and a three carbon methylene spacer.

In generic formulae the building units are abbreviated as R with a superscript corresponding to the position in the sequence preceded by the letter N, as an indication that the backbone nitrogen at that position is the attachment point of the bridging group specified in said formulae.

As used herein "backbone cyclic peptide" denotes an analog of a linear peptide which contains at least one building unit that has been liked to form a bridge via the alpha nitrogen of the peptide backbone to another building unit, or to another amino acid in the sequence.

Certain abbreviations are used herein to describe this invention and the manner of making and using it. For instance, AcOH refers to acetic acid, Alloc refer to allyloxycarbonyl, Boc refers to the t-butyloxycarbonyl radical, BOP refers to benzotriazol-1-yloxy-tris-(dimethylamino)phosphonium hexafluorophosphate, DCC refers to dicyclohexylcarbodiimide, DCM refers to dichloromethane, DIEA refers to the diisopropyl-ethul amine, DIEA refers to diisopropyl-ethyl amine, DMF refers to dimethyl formamide, EDT refers to ethanedithiol, Fmoc refers to the fluorenyhnethoxycarbonyl radical, GH refers to growth hormone, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, IGF refers to insulin growth factor, MS refers to mass spectrometry, NIDDM refers to Non Insulin Dependent Diabetes Mellitus, NMM refers to N-methylmorpholine, NMP refers to 1-methyl-2-pyrolidonone, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, rt refers to room temperature, SRIF refers to Somatotropin Release Inhibitory Factor, TBTU refers to 2-(1H-benzotriazole-1-yl)-1,1,3,3-tetramethyluronium tetrafluoroborate, t-Bu refers to the tertiary butyl radical, and VIP refers to vasoctive intestinal peptide.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, β-Ala refers to β-Alanine, ChxGly refers to cyclohexyl Glycine, Dab refers to Di amino butyric acid, GABA refers to gama amino butyric acid, Hcys refer to homocystein, p-Cl)Phe refers to para chloro Phenylalanine, (p-NH$_2$)Phe refers to para amino Phenylalanine, (p-F)Phe refers to para fluoro Phenylalanine, (p-NO$_2$)Phe refers to para nitro Phenylalanine, 1Nal refers to 1-naphthylalanine, 2Nal refers to 2-naphthylalanine, Nva refers to norvaline, Thi refers to thienylalanine.

Conservative substitution of amino acids as know to those skilled in the art are within the scope of the present invention. Conservative amino acid substitutions includes replacement of one amino acid with another having the same type of functional group or side chain e.g. aliphatic, aromatic, positively charged, negatively charged. These substitutions also include replacement of Phe residues with N-Methyl-Phe residues for increasing the bio-availability of the compound and conjugation of mono- and di-saccharide moieties at the amino terminus for increasing oral bio-availability (Nelson-Piercy et al. *J. Clin. Endocrinol. And Metab.* 78:329, 1994), or other such substitutions as may enhance oral bioavailability, penetration into the central nervous system, targeting to specific cell populations and the like.

Synthetic Approaches

According to the present invention peptide analogs are cyclized via bridging groups attached to the alpha nitrogens of amino acids that permit novel non-peptidic linkages. In general, the procedures utilized to construct such peptide analogs from their building units rely on the known principles of peptide synthesis; most conveniently, the procedures can be performed according to the known principles of solid phase peptide synthesis. The innovation requires replacement of one or more of the amino acids in a peptide sequence by novel building units of the general Formula:

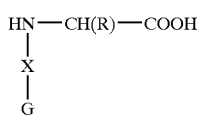

Formula No. 6 wherein R is the side chain of an amino acid, X is a spacer group and G is the functional end group by means of which cyclization will be effected. The side chain R is the side chain of any natural or synthetic amino acid that is selected to be incorporated into the peptide sequence of choice. X is a spacer group that is selected to provide a greater or lesser degree of flexibility in order to achieve the appropriate conformational constraints of the peptide analog. Such spacer groups include alkylene chains, substituted, branched and unsaturated alkylenes, arylenes, cycloalkylenes, and unsaturated and substituted cycloalkylenes. Furthermore, X and R can be combined to form a heterocyclic structure.

The terminal (ω) functional groups to be used for cyclization of the peptide analog include but are not limited to:

a. Amines, for reaction with electrophiles such as activated carboxyl groups, aldehydes and ketones (with or without subsequent reduction), and alkyl or substituted alkyl halides.

b. Alcohols, for reaction with electrophiles such as activated carboxyl groups.

c. Thiols, for the formation of disulfide bonds and reaction with electrophiles such as activated carboxyl groups, and alkyl or substituted alkyl halides.

d. 1,2 and 1,3 Diols, for the formation of acetals and ketals.

e. Alkynes or Substituted Alkynes, for reaction with nucleophiles such as amines, thiols or carbanions; free radicals; electrophiles such as aldehydes and ketones, and alkyl or substituted alkyl halides; or organometallic complexes.

f. Carboxylic Acids and Esters, for reaction with nucleophiles (with or without prior activation), such as amines, alcohols, and thiols.

g. Alkyl or Substituted Alkyl Halides or Esters, for reaction with nucleophiles such as amines, alcohols, thiols, and carbanions (from active methylene groups such as acetoacetates or malonates); and formation of free radicals for subsequent reaction with alkenes or substituted alkenes, and alkynes or substituted alkynes.

h. Alkyl or Aryl Aldehydes and Ketones for reaction with nucleophiles such as amines (with or without subsequent reduction), carbanions (from active methylene groups such as acetoacetates or malonates), diols (for the formation of acetals and ketals).

i. Alkenes or Substituted Alkenes, for reaction with nucleophiles such as amines, thiols, carbanions, free radicals, or organometallic complexes.

j. Active Methylene Groups, such as malonate esters, acetoacetate esters, and others for reaction with electrophiles such as aldehydes and ketones, alkyl or substituted alkyl halides.

It will be appreciated that during synthesis of the peptide these reactive end groups, as well as any reactive side chains, must be protected by suitable protecting groups.

Suitable protecting groups for amines are alkyloxy, substituted alkyloxy, and aryloxy carbonyls including, but not limited to, tert butyloxycarbonyl (Boc), Fluorenylmethyloxycarbonyl (Fmoc), Allyloxycarbonyl (Alloc) and Benzyloxycarbonyl (Z).

Carboxylic end groups for cyclizations may be protected as their alkyl or substituted alkyl esters or thio esters or aryl or substituted aryl esters or thio esters. Examples include but are not limited to tertiary butyl ester, allyl ester, benzyl ester, 2-(trimethylsilyl)ethyl ester and 9-methyl fluorenyl.

Thiol groups for cyclizations may be protected as their alkyl or substituted alkyl thio ethers or disulfides or aryl or substituted aryl thio ethers or disulfides. Examples of such groups include but are not limited to tertiary butyl, trityl (triphenylmethyl), benzyl, 2-(trimethylsilyl)ethyl, pixyl(9-phenylxanthen-9-yl), acetamidomethyl, carboxymethyl, 2-thio-4-nitropyridyl.

It will further be appreciated by the artisan that the various reactive moieties will be protected by different protecting groups to allow their selective removal. Thus, a particular amino acid will be coupled to its neighbor in the peptide sequence when the $N^\alpha$ is protected by, for instance, protecting group A. If an amine is to be used as an end group for cyclization in the reaction scheme the $N^\omega$ will be protected by protecting group B, or an ε amino group of any lysine in the sequence will be protected by protecting group C, and so on.

The coupling of the amino acids to one another is performed as a series of reactions as is known in the art of peptide synthesis. Novel building units of the invention, namely the $N^\alpha$-ω-functionalized amino acid derivatives are incorporated into the peptide sequence to replace one or more of the amino acids. If only one such $N^\alpha$-ω-functionalized amino acid derivative is selected, it will be cyclized to a side chain of another amino acid in the sequence or to either of the two terminal amino acids of the peptide sequence. For instance: (a) an $N^\alpha$-(ω-amino alkylene) amino acid can be linked to the carboxyl group of an aspartic or glutamic acid residue; (b) an $N^\alpha$-(ω-carboxylic alkylene) amino acid can be linked to the ε-amino group of a lysine residue; (c) an $N^\alpha$-(ω-thio alkylene) amino acid can be linked to the thiol group of a cysteine residue; and so on. A more preferred embodiment of the invention incorporates two such $N^\alpha$-ω-functionalized amino acid derivatives which may be linked to one another to form N-backbone to N-backbone cyclic peptide analogs. Three or more such building units can be incorporated into a peptide sequence to create bicyclic peptide analogs as will be elaborated below.

Thus, peptide analogs can be constructed with two or more cyclizations, including N-backbone to N-backbone, as well as backbone to side-chain or any other peptide cyclization.

As stated above, the procedures utilized to construct somatostatin analogs of the present invention from novel building units generally rely on the known principles of peptide synthesis. However, it will be appreciated that accommodation of the procedures to the bulkier building units of the present invention may be required. Coupling of the amino acids in solid phase peptide chemistry can be achieved by means of a coupling agent such as but not limited to dicyclohexycarbodiimide (DCC), bis(2-oxo-3-oxazolidinyl) phosphinic chloride (BOP-Cl), benzotriazolyl-N-oxytrisdimethyl-aminophosphonium hexafluoro phosphate (BOP), 1-oxo-1-chlorophospholane (Cpt-Cl), hydroxybenzotriazole (HOBT), or mixtures thereof.

It has now been found that coupling of the subsequent amino acid to the bulky building units of the present invention may require the use of additional coupling reagents including, but not limited to: coupling reagents such as PyBOP (Benzotriazole-1-yl-oxy-tris-pyrrolidino-phosphonium hexafluorophosphate), PyBrOP (Bromo-tris-pyrrolidino-phosphonium hexafluorophosphate), HBTU (2-(1H-Benzotriazole-1-yl)-1,1,3,3-tetramethyluronium hexafluoro-phosphate), TBTU (2-(1H-Benzotriazole-1-yl)-1,1,3,3-tetramethyluronium tetrafluoroborate).

Novel coupling chemistries may be used, such as preformed urethane-protected N-carboxy anhydrides (UNCA'S), preformed acyl halides most preferably acyl chlorides.

Advantageously, it is also possible to use in situ generated amino acid chlorides. The amino acid chlorides could be generated by utilizing reagents such as bis-(trichloromethyl) carbonate, commonly known as triphosgene, for example.

Such coupling may take place at room temperature and also at elevated temperatures, in solvents such as toluene, DCM (dichloromethane), DMF (dimethylformamide), DMA (dimethylacetamide), NMP (N-methyl pyrrolidinone), dioxane, tetrahydrofuran, diglyme and 1,3 dichloropropane, or mixtures of the above.

The preferred backbone cyclized somatostatin analogs of the present invention are now described.

One embodiment has the following formula:

Formula No. 7

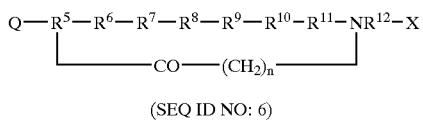

(SEQ ID NO: 6)

wherein n is 1 to 5;

X designates a terminal carboxy acid, amide or alcohol group;

Q is hydrogen or a mono- or di-saccharide;

$R^5$ is gamma amino butyric acid, diamino butyric acid, Gly, α-Ala, 5-amino pentanoic acid or amino hexanoic acid;

$R^6$ is (D)- or (L)-Phe or Tyr;

$R^7$ is (D)- or (L)-Trp, (D)- or (L)-Phe, (D)- or (L)-1Nal or (D)- or (L)-2Nal, or Tyr;

$R^8$ is (D)- or (L)-Trp;

$R^9$ is (D)- or (L)-Lys;

$R^{10}$ is Thr, Gly, Abu, Ser, Cys, Val, (D)- or (L)-Ala, or (D)- or (L)-Phe;

$R^{11}$ is (D)- or (L)-Phe, (D)- or (L)-Ala, Nle, or Cys; and $R^{12}$ is Gly, Val, Leu, (D)- or (L)-Phe or 1Nal or 2Nal;

A most preferred compound according to this embodiment is denoted PTR 3173 wherein the residues are as follows:

Q is hydrogen;

$R^5$ is GABA;

$R^6$ is Phe;

$R^7$ is Trp;

$R^8$ is (D)Trp;

$R^9$ is Lys;

$R^{10}$ is Thr;

$R^{11}$ is Phe;

$R^{12}$ is Gly;

n is 3; and

X is an amide.

Another preferred compound according to this embodiment is denoted PTR 3229 wherein the residues are as follows:

Q is galactose;

$R^5$ is Dab;

$R^6$ is Phe;

$R^7$ is (L)-Trp;

$R^8$ is (D) Trp;

$R^9$ is Lys;

$R^{10}$ is Thr;

$R^{11}$ is Phe;

$R^{12}$ is Gly;

n is 3; and

X is amide.

Another embodiment has the general formula:

Formula No. 8

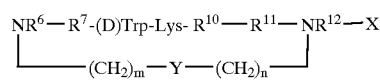

wherein:

m and n are 1 to 5

X designates a terminal carboxy acid, amide or alcohol group;

$R^6$ is(D)- or (L)-Phe, or (D)- or (L)-Ala;

$R^7$ is Tyr, (D)- or (L)-Ala, or (D)- or (L)-Phe;

$R^{10}$ is Thr, Val, Ser, or Cys;

$R^{11}$ is Val, (D)- or (L)-1Nal, (D)- or (L)-2Nal, or (D) or (L)-Phe;

$R^{12}$ is Gly, (D)- or (L)-Ala, or (D) or (L)-Phe; and $Y^2$ is amide, thioether, thioester or disulfide.

Preferably:

$R^6$ is (D)- or (L)-Phe;

$R^7$ is Tyr or Phe;

$R^{10}$ is Thr, Val or Ser;

$R^{11}$ is Val, 1Nal or 2Nal;

$R^{12}$ is Gly; and $Y^2$ is amide.

Yet another embodiment has the general formula:

Formula No. 9

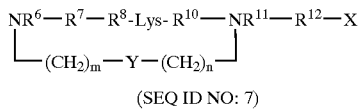

(SEQ ID NO: 7)

wherein:
m and n are 1 to 5;
X designates a terminal carboxy acid, amide or alcohol group;
$R^6$ is (D)- or (L)-Phe, or (D)- or (L)-Ala;
$R^7$ is Tyr or (D)- or (L)-Phe;
$R^8$ is (D)- or (L)-Trp, (D)- or (L)-1Nal or (D)- or (L)-2Nal,
$R^{10}$ is Thr, Val, Ser, or Cys;
$R^{11}$ is Gly or (D) or (L)-Phe;
$R^{12}$ is Thr, GABA, (D)- or (L)-1Nal, (D)- or (L)-2Nal, or (D) or (L)-Phe; and
$Y^2$ is amide, thioether, thioester or disulfide.
Preferably,
$R^6$ is (D)- or (L)-Phe;
$R^7$ is Tyr;
$R^8$ is (D)Trp, (D)1Nal or (D)2Nal;
$R^{10}$ is Val;
$R^{11}$ is Gly;
$R^{12}$ is Thr, 1Nal or 2Nal; and
$Y^2$ is amide.
One more preferred embodiment has the following formula:

Formula No. 10

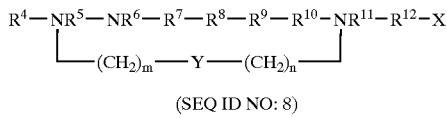

(SEQ ID NO: 8)

wherein
m and n are 1 to 5,
X designates a terminal carboxy acid, amide or alcohol group,
$R^4$ is absent or is a terminal group of one to four amino acids;
$R^5$ is 1Nal, 2Nal, beta-Asp (Ind), Gly, Tyr, (D)- or (L)-Ala, or (D)- or (L)-Phe;
$R^6$ and $R^7$ may be absent, or are independently Gly, Tyr, (D)- or (L)-Ala, or (D)- or (L)-Phe;
$R^8$ is (D)- or (L)-Trp,
$R^9$ is (D)- or (L)-Lys;
$R^{10}$ is absent or is Gly, Abu, Cys, Thr, Val, (D)- or (L)-Ala, or (D)- or (L)-Phe;
$R^{11}$ is Cys, (D)- or (L)-Ala, or (D)- or (L)-Phe;
$R^{12}$ is absent or is Val, Thr, 1Nal or 2Nal; and
$Y^2$ is amide, thioether, thioester or disulfide.
Preferably:
$R^4$ is absent;
$R^5$ is (D)- or (L)-Phe, or (D)- or (L)-Ala;
$R^6$ may be absent and $R^6$, when present, and $R^7$ are independently (D)- or (L)-Phe, Ala or Tyr;

$R^{10}$ is absent or is Thr, Val or (D)- or (L)-Phe,
$R^{11}$ is (D)- or (L)-Ala, or (D)- or (L)-Phe, and
$R^{12}$ is absent.
Alternatively:
$R^5$ is (D)- or (L)-Ala, or (D)- or (L)-Phe;
$R^6$ is absent or is (D)- or (L)-Ala, or (D)- or (L)-Phe,
$R^7$ is (D)- or (L)-Ala, or (D)- or (L)-Phe,
$R^{10}$ is absent or is Thr, Cys, (D)- or (L)-Ala;
$R^{11}$ is Cys, (D)- or (L)-Ala, or (D)- or (L)-Phe; and
$R^{12}$ is absent or is Thr.
Another embodiment has the general formula:

Formula No. 11

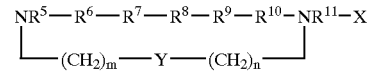

(SEQ ID NO: 9)

wherein:
m and n are 1 to 5,
$R^5$ is (L)- or (D)-Phe, Tyr or (D)- or (L)-Ala;
$R^6$ is (L)- or (D)-Phe, Tyr or (D)- or (L)-Ala;
$R^7$ is absent or is (D)- or (L)-Phe, Tyr, or (D)- or (L)-Ala,
$R^8$ is (D)- or (L)-Trp;
$R^9$ is (D)- or (L)-Lys,
$R^{10}$ is absent or is Thr, Val, Cys or (D)- or (L)-Ala,
$R^{11}$ is (L)- or (D)-Phe, Cys, (D)- or (L)-Ala;
$Y^2$ is amide, thioether, thioester or disulfide.
Preferably
$R^6$ is (D)- or (L)-Ala;
$R^7$ is absent or is (D)- or (L)-Phe;
$R^{10}$ is Thr,
$R^{11}$ is Cys; and
X is an alcohol group.
Yet another embodiment has the general formula Formula No. 12

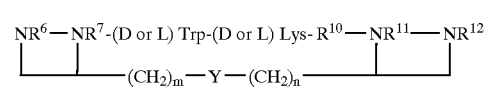

(SEQ ID NO: 10)

wherein:
the dotted line indicates that the bridge is connected to $NR^6$ or $NR^7$ at one end and to $NR^{11}$ or $NR^{12}$ at the other end;
$R^6$ is absent or is (D)- or (L)-Phe or Ala,
$R^7$ is (D)- or (L)-Phe, Ala or Tyr;
$R^8$ is Thr, Ala, Val or Cys;
$R^{11}$ is absent or is (D)- or (L)-Phe, Ala or Cys;
$R^{12}$ is absent or is Thr or Thr reduced to an alcohol; and
$Y^2$ is amide, thioether, thioester or disulfide
Preferably, the bridge is connected to $NR^6$ and $NR^{11}$ or to $NR^6$ and $NR^{12}$ with $R^{12}$ being Thr reduced to an alcohol.

Another preferred embodiment has the general formula:

Formula No. 13

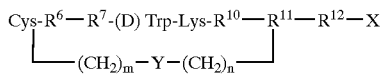

wherein m and n are 1 to 5;
- X designates a terminal carboxy acid, amide or alcohol group;
- $R^6$ is (D)- or (L)-Phe or Tyr;
- $R^7$ is (D)- or (L)-Trp, (D)- or (L)-Phe, (D)- or (L)-1Nal or (D)- or (L)-2Nal, or Tyr;
- $R^{10}$ is Thr, Gly, Abu, Ser, Cys, Val, (D)- or (L)-Ala, or (D)- or (L)-Phe;
- $R^{11}$ is (D)- or (L)-Phe or (D)- or (L)-Ala;
- $R^{12}$ is Gly, Val, or (D)- or (L)-Phe; and
- $Y^2$ is thioether, thioester or disulfide.

Preferably:
- $R^6$ is Phe;
- $R^7$ is Trp;
- $R^{10}$ is Thr;
- $R^{11}$ is Phe;
- $R^{12}$ is Gly; and
- $Y^2$ is disulfide.

Another preferred embodiment has the general formula:

Formula No. 14

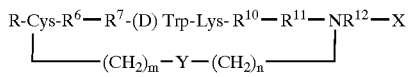

wherein m and n are 1 to 5;
- X designates a terminal carboxy acid, amide or alcohol group;
- $R^4$ is (D)- or (L)-Phe or Tyr;
- $R^6$ is (D)- or (L)-Phe or Tyr;
- $R^7$ is (D)- or (L)-Trp, (D)- or (L)-Phe, (D)- or (L)-1Nal or (D)- or (L)-2Nal, or Tyr;
- $R^{10}$ is Thr, Gly, Abu, Ser, Cys, Val, (D)- or (L)-Ala, or (D)- or (L)-Phe;
- $R^{11}$ is (D)- or (L)-Phe or (D)- or (L)-Ala;
- $R^{12}$ is Gly, Val, or (D)- or (L)-Phe or is absent; and
- $Y^2$ is thioether, thioester or disulfide.

Preferably:
- $R^4$ is (D)Phe;
- $R^6$ is Phe;
- $R^7$ is Trp;
- $R^{10}$ is Thr;
- $R^{11}$ is Phe;
- $R^{12}$ is Gly; and
- $Y^2$ is disulfide.

Another more preferred embodiment has the general formula:

Formula No. 15

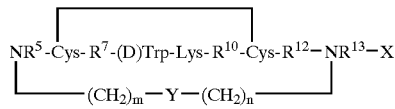

wherein m and n are 1 to 5;
- X designates a terminal carboxy acid, amide or alcohol group;
- $R^5$ is (D)- or (L)-Phe or (D)- or (L)-Ala;
- $R^7$ is (D)- or (L)-Trp, (D)- or (L)-Phe, (D)- or (L)-1Nal or (D)- or (L)-2Nal, or Tyr;
- $R^{10}$ is Thr, Gly, Abu, Ser, Cys, Val, (D)- or (L)-Ala, or (D)- or (L)-Phe;
- $R^{12}$ is Gly, Val, (D)- or (L)-Phe or is absent;
- $R^{13}$ is (D)- or (L)-Phe or (D)- or (L)-Ala; and
- $Y^2$ is amide, thioether, thioester or disulfide.

Preferably:
- $R^5$ is Phe;
- $R^7$ is Phe;
- $R^{10}$ is Thr;
- $R^{12}$ is Gly, Val, or (D)- or (L)-Phe;
- $R^{13}$ is Phe; and
- $Y^2$ is amide.

Additional preferred embodiments were synthesized using multiple peptide parallel synthesis (under the name TY-30005) comprise heptapeptide and octapeptide analogs in four groups (A–D) as described below.

Group A:

Formula No. 16

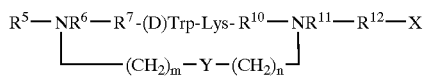

wherein:
- m and n are 1 to 5;
- X designates a terminal carboxy acid, amide or alcohol group;
- $R^5$ is absent or is 2Nal;
- $R^6$ is Phe(N2) or Gly(N3);
- $R^7$ is (p-Cl)Phe, (p-NH$_2$)Phe, (p-F)Phe, (p-NO$_2$)Phe or ChxGly;
- $R^{10}$ is Val, Gly, or (D)ChxGly;
- $R^{11}$ is Trp(C3) or GlyC2;
- $R^{12}$ is 2Nal or Thr;
- $Y^2$ is amide, thioether, thioester or disulfide.

Group B:

Formula No. 17

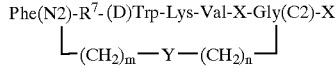

wherein:
- m and n are 1 to 5;

X designates a terminal carboxy acid, amide or alcohol group;
$R^7$ is (p-Cl)Phe, (p-NH$_2$)Phe, (p-NO$_2$)Phe, or Tyr;
$R^{11}$ is Ile, Val or Ala;
$Y^2$ is amide.

Group C:

Formula No. 18

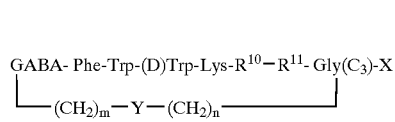

wherein:
m and n are 1 to 5;
X designates a terminal carboxy acid, amide or alcohol group;
$R^{10}$ is Ala, Abu, Nle, Val or Thr;
$R^{11}$ is Phe, Tyr, (p-Cl)Phe, (p-NH$_2$)Phe, (p-NO$_2$)Phe or (p-F)Phe;
$Y^2$ is amide, thioether or thioester.

X designates a terminal carboxy acid, amide or alcohol group;

$R^6$ is Val, Phe, (p-F)Phe or (p-Cl)Phe;

$R^7$ is Trp, Tyr, (p-Cl)Phe, (p-NH$_2$)Phe, (p-F)Phe, (p-NO$_2$) Phe or ChxGly;

$R^{11}$ is Val or ChxGly;

$Y^2$ is amide.

The preferred analogs of the multiple parallel synthesis group are described in table 2 below:

TABLE 2

Preferred multiple parallel synthesis (TY-30005) sequences.

| Pep No. | \multicolumn{9}{c}{Position is SRIF sequence} | group |
|---|---|---|---|---|---|---|---|---|---|---|
| | 5 | 6 | 7 | 8 | 9 | 10 | 11 | 12 | 13 | |
| 5 | | Phe(N2) | (p-NH$_2$)Phe | (D)Trp | Lys | Val | Gly(C2) | 2Nal | | A |
| 6 | | Phe(N2) | (p-Cl)Phe | (D)Trp | Lys | Val | Gly(C2) | 2Nal | | |
| 7 | | Phe(N2) | (p-F)Phe | (D)Trp | Lys | Val | Gly(C2) | 2Nal | | |
| 8 | | Phe(N2) | (p-NO$_2$)Phe | (D)Trp | Lys | Val | Gly(C2) | 2Nal | | |
| 35 | | Phe(N2) | (p-Cl)Phe | (D)Trp | Lys | Gly | Trp(C3) | Thr | | |
| 72 | 2Nal | Gly(N3) | ChxGly | (D)Trp | Lys | (D)ChxGly | Gly(C2) | Thr | | |
| 22 | | Phe(N2) | Tyr | (D)Trp | Lys | Val | Ile | Gly(C2) | | B |
| 27 | | Phe(N2) | (p-NH$_2$)Phe | (D)Trp | Lys | Val | Val | Gly(C2) | | |
| 28 | | Phe(N2) | (p-Cl)Phe | (D)Trp | Lys | Val | Ala | Gly(C2) | | |
| 30 | | Phe(N2) | (p-NO$_2$)Phe | (D)Trp | Lys | Val | Val | Gly(C2) | | |
| 52 | GABA | Phe | Trp | (D)Trp | Lys | Ala | Phe | Gly(C3) | | C |
| 53 | GABA | Phe | Trp | (D)Trp | Lys | Abu | Phe | Gly(C3) | | |
| 56 | GABA | Phe | Trp | (D)Trp | Lys | Nle | Phe | Gly(C3) | | |
| 58 | GABA | Phe | Trp | (D)Trp | Lys | Val | Phe | Gly(C3) | | |
| 61 | GABA | Phe | Trp | (D)Trp | Lys | Thr | Phe | Gly(C3) | | |
| 62 | GABA | Phe | Trp | (D)Trp | Lys | Thr | (p-NH$_2$)Phe | Gly(C3) | | |
| 63 | GABA | Phe | Trp | (D)Trp | Lys | Thr | (p-Cl)Phe | Gly(C3) | | |
| 64 | GABA | Phe | Trp | (D)Trp | Lys | Thr | (p-F)Phe | Gly(C3) | | |
| 65 | GABA | Phe | Trp | (D)Trp | Lys | Thr | (p-NO$_2$)Phe | Gly(C3) | | |
| 66 | GABA | Phe | Trp | (D)Trp | Lys | Thr | Tyr | Gly(C3) | | |
| 83 | b-Ala | (p-Cl)Phe | Trp | (D)Trp | Lys | Thr | ChxGly | GlyC3 | (D)Phe | D |
| 84 | b-Ala | (p-F)Phe | Trp | (D)Trp | Lys | Thr | ChxGly | GlyC3 | (D)Phe | |
| 88 | b-Ala | Val | Trp | (D)Trp | Lys | Thr | ChxGly | GlyC3 | (D)Phe | |
| 89 | b-Ala | Phe | Tyr | (D)Trp | Lys | Thr | Val | GlyC3 | (D)Phe | |
| 90 | b-Ala | Phe | (p-NO$_2$)Phe | (D)Trp | Lys | Thr | Val | GlyC3 | (D)Phe | |
| 91 | b-Ala | Phe | (p-Cl)Phe | (D)Trp | Lys | Thr | Val | GlyC3 | (D)Phe | |
| 92 | b-Ala | Phe | (p-F)Phe | (D)Trp | Lys | Thr | Val | GlyC3 | (D)Phe | |
| 93 | b-Ala | Phe | (p-NH$_2$)Phe | (D)Trp | Lys | Thr | Val | GlyC3 | (D)Phe | |
| 94 | b-Ala | Phe | ChxGly | (D)Trp | Lys | Thr | Val | GlyC3 | (D)Phe | |

Group D:

Formula No. 19

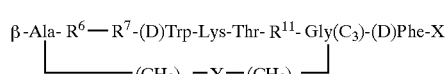

wherein:

m and n are 1 to 5;

The most preferred backbone cyclized somatostatin analogs of the invention described in table 3:

TABLE 3

The most preferred analogs.

| PTR | Sequence |
|---|---|
| 3171 | Phe*-Phe-Phe-(D)Trp-(D)Lys-Phe(C2)-X |
| 3113 | Phe(C1)-Phe-Phe-(D)Trp-Lys-Phe(N2)-X |
| 3123 | Phe(C1)-Phe-Phe-(D)Trp-(D)Lys-Phe(N2)-X |

TABLE 3-continued

The most preferred analogs.

| PTR | Sequence |
| --- | --- |
| 3209 | Phe(N2)-Tyr-(D)2Nal-Lys-Val-Gly(C2)-Thr-X |
| 3183 | Phe(N2)-Tyr-(D)Trp-Lys-Val-Gly(C2)-2Nal-X |
| 3185 | Phe(N2)-Tyr-(D)Trp-Lys-Val-Val-Gly(C2)-X |
| 3201 | Phe(N2)-Tyr-(D)Trp-Lys-Ser-2Nal-Gly(C2)-X |
| 3203 | Phe(N2)-Phe-(D)Trp-Lys-Thr-2Nal-Gly(C2)-X |
| 3173 | GABA*-Phe-Trp-(D)Trp-Lys-Thr-Phe-Gly(C3)-X |
| 3197 | Cys*-Phe-Trp-(D)Trp-Lys-Thr-Phe-Gly(S2)-X |
| 3205 | Phe(C3)-Cys*-Phe-(D)Trp-Lys-Thr-Cys*-Phe(N3)-X |
| 3207 | (D)Phe-Cys*-Phe-Trp-(D)Trp-Lys-Thr-Phe-Gly(S2)-X |
| 3229 | Galactose-Dab*-Phe-Trp-(D)Trp-Lys-Thr-Phe-Gly(C3)-X | where X is —NH$_2$ or —OH and the bridging group extends between the two building units or as indicated below: For PTR 3171 and PTR 3173, the asterisk denotes that the bridging group is connected between the N$^\alpha$-ω-functionalized derivative of an amino acid and the N terminus of the peptide. For PTR 3197 and PTR 3207, the asterisk denotes that the bridging group is connected between the N$^\alpha$-ω-functionalized derivative of an amino acid and the side chain of the Cys residue. PTR 3205 is a bicyclic compound in which one bridge connects the two building units (Phe-C3 and Phe-N3) and the second is a disulfide bridge formed between the two Cys residues.

Somatostatin is a tetradecapeptide hormone whose numerous regulatory functions are mediated by a family of five receptors, whose expression is tissue dependent. Receptor specific analogs of somatostatin are believed to be valuable therapeutic agents in the treatment of various diseases. Attempts to design small peptide analogs having this selectivity have not been highly successful. It has now unexpectedly been found that the conformationally constrained backbone cyclized somatostatin analogs of the present invention, are highly selective to SST receptor subtypes.

The backbone cyclic peptides of this invention are novel selective analogs and preferably bind with higher affinity to a single receptor of the somatostatin receptor family. PTR 3113 and PTR 3123 are selective for the type 3 somatostatin receptor previously studied analogs have failed to achieve specificity to this receptor subtype. PTR 3183, 3185 and 3201 are selective for the type 5 somatostatin receptor. PTR 3209 is selective for the type 1 receptor. PTR 3203 is selective for receptors 3 and 5, and PTR 3173 is selective for receptors 2 and 5. PTR 3205 is a bicyclic analog which is selective to somatostatin receptor type 2.

The amino acid sequence of the corresponding backbone hexacyclic analogs (PTRs 3113, 3123 and 3171)is based on what are believed to be the most important amino acids derived from the native SRIF-14. From the data in the literature (SMS 210–995: A very potent and selective octapeptide analogue (i.e., Octreotide) of somatostatin having prolonged action, (Bauer, et al. *Life Sciences*, 31:1133, 1982), it was concluded that the amino acids of the native SRIF-14 in at least positions seven through 10, namely 7-Phe, 8-Trp, 9-Lys, and 10-Thr, and preferably positions six through 10, namely 6-Phe, 7-Phe, 8-Trp, 9-Lys, and 10-Thr, are essential to the pharmacophore of the hormone.

The present innovative backbone analogs preferably include 5 to 8 amino acids with special amine acid modifications. For certain preferred analogs, the amino acid Asn was substituted by the backbone Phe building unit at position 5. The configuration substitution of the native L-Trp at position 8 to D-Trp was made to improve the stability of the analog. The Thr residue at position 10 was deleted and the sequence completed by the corresponding backbone Phe building unit. The unique configuration substitution at position 9 from L-Lys to D-Lys as shown in PTRs 3123 and 3171 in comparison to PTR 3113 imparts improved selectivity of binding to the SST receptor subtype SSTR3 rather than SSTR5.

In additional more preferred analogs further modification of amino acids were performed. For example substitution of Phe residues with Tyr for facilitating Iodination. Substitution of Phe residues with N-Methyl-Phe residue (for example substitution of Phe$^6$ in PTR 3173 to yield PTR 3223 and substitution of Phe$^6$ and Phe$^{11}$ in PTR 3173 to yield PTR 3225) for increasing the bio-availability of the compound. Addition of mono- and di-saccharides moieties at the amino terminus of certain compounds is performed for increasing the oral bio-availability (Nelson-Piercy et al. ibid.). For example galactose was conjugated to the N-terminal of compound similar to PTR 3173 to yield an analog having the sequence:

Galactose-Dab-Phe-Trp-(D)Trp-Lys-Thr-Phe-Gly(C3)-NH$_2$ denoted herein PTR 3229

In certain most preferred analogs (PTR 3171 and 3173 for example) the bridge is connected between N$^\alpha$-ω-functionalized derivative of an amino acid and the N-terminus of the peptide sequence. For other preferred analogs of the present invention the bridge is connected between a building unit comprising an N$^\alpha$-ω functionalized derivative having a terminal thio group and another such derivative of an amino acid, or to the side chain of a Cys residue, to a mercapto-containing acid or to any other SH containing moiety to form a disulfide bridge.

The present novel analogs provide an additional dimension to the novelty of the backbone cyclization technology, in the utilization of a shortened backbone bridge (i.e., only one to three methylenes beside the peptide bond). This approach enables one to obtain much greater rigidity of the peptide, and to further constrain the desired conformation of the native pharmacophore.

An additional advantage of the hexapeptide analogs is related to their relative low molecular weight (their sequence consisting of only six amino acids), up to only 1000 daltons, in comparison to the most common somatostatin synthetic analogs which usually are hepta or octapeptides.

Backbone cyclic somatostatin analogs of the present invention (for example PTR 3123, 3173, 3201 and 3205) were found to possess considerable metabolic bio-stability against degradation by enzymes. This attribute could suggest a potentially long duration of activity in the body. The stability of the backbone cyclic analogs was comparable to that of the metabolically stable drug Octreotide using experimental stability measurements based on degradation by various enzyme mixtures (e.g. renal homogenate, rat liver homogenate and human serum). All tested compounds showed significantly higher bio-stability than the native hormone SRIF-14. In some of the corresponding non-cyclized peptides, some degradation was observed two hours after incubation, which indicated that the cyclization remarkably contributed to the stability of the peptide. The incorporation of the N-alkylated amino acids used for the backbone cyclization was expected to confer metabolic bio-stability to these peptides.

Backbone cyclic analogs of the present invention bind in-vitro with high affinity to a defined subset of the human somatostatin receptors. This receptor selectivity indicates its potential physiological selectivity in-vivo.

Consistent with the in-vitro receptor binding, backbone cyclic analogs of the present invention selectively affects a defined system in the body while not affecting other known physiological activities of the native hormone somatostatin. For example, PTR 3173 exerts significant inhibition with prolonged duration of action on the Growth Hormone-IGF-1 axis of a similar magnitude as the drug Octreotide, but it lacks the disadvantages of Octreotide such as inhibition of Insulin secretion. PTR 3173 also has a considerably lower affect on the release of glucagon than Octreotide, it thus has the advantage of not causing hyperglycemia which makes it a very attractive compound for the treatment of Diabetes Type 2 (NIDDM).

As summarized in table 4 PTR 3173 possesses significant physiological selectivity over the drug Octreotide. PTR 3173 is a potent inhibitor of growth hormone but has much less activity on glucagon, and no considerable effect on insulin.

TABLE 4

Physiological Selectivity of PTR 3173 in comparison to Octreotide.

| Analog | GH ID50 µg/kg | Glucagon ID50 µg/kg | Insulin ID50 µg/kg | GH/Insulin | GH Glucagon |
|---|---|---|---|---|---|
| Octreotide | 0.08 | 0.65 | 26 | 309 | 8 |
| PTR 3173 | 0.1 | >100 | >1000 | >10,000 | >1,000 |

TABLE 5

Main pharmacokinetic parameters of PTR 3173 vs. Octreotide following IV & SC administration to Conscious Wistar rats.

| Route | Drug | F (%) | Vss (ml/kg) | T½β (min) | E % | Clearance (ml/min/kg) |
|---|---|---|---|---|---|---|
| IV | PTR 3173 | — | 653 | 31 | 10.3 | 13.0 |
|  | Octreotide* | — | 602 | 49 | 21.3 | 17.6 |
| SC | PTR 3173 | 99.6 | — | 170 | 15.9 | 13.3 |
|  | Octreotide* | 103 | — | 40 | 23.0 | 17.1 |

*From Sandostatin (Octreotide acetate), Overview and clinical summary. Sandoz Pharmaceutical Corporation, 1992.
F - Bioavailability, Vs. - Volume of distribution, T½ - circulating half life, E - Extracted in urine The backbone cyclic somatostatin analog PTR 3173 is selective to somatostatin receptors and binds significantly less other G-protein coupled receptors than Octreotide as PTRs 3123 inhibits only the release of glucagon secretion but not growth hormone or insulin which makes it a potential therapeutic agent for glucagonoma with no adverse effects on the release of growth hormone and insulin. In addition, it is an anticancer candidate for malignancies expressing SST-R3 only. The native hormone SRIF as well as its synthetic analog Octreotide, inhibit simultaneously growth hormone, glucagon and insulin and therefore they are not selective.

PTR 3205 is a bicyclic compound in which one bridge connects the two building units and the second is a disulfide bridge formed between two Cys residues. This analog is selective for somatostatin receptor 2 and thus it is an anticancer candidate for imaging and treating malignancies expressing this receptor subtype without influencing other somatostatin receptor activities. Similarly, analogs such as PTR 3201 are selective to somatostatin receptor 5 and are thus candidates for imaging the therapy of malignancies expressing this receptor subtype.

PTR 3173 shows a significant growth inhibition of CHO-cells expressing cloned human SST-R5, indicating a potential role in the treatment of SST-R5 expressing tumors (e.g. carcinoids, pituitary tumors). This analog also inhibits Chromogranin A release from the human Carcinoid cell line, indicating an anti-tumor effect (example 5).

The unique pharmacokinetic profile of PTR 3173 as evaluated in animals is consistent with its metabolic biostability as evaluated in-vitro. This backbone cyclic somatostatin analog displays flip flop (a slow release kinetic) pharmacokinetcs. Following subcutaneous administration, the apparent curculatory half life resulting from its rate of absorption but not from its rate of elimination. Following subcutaneouos administration to rats, PTR 3173 had a circulatory half-life of about 3 hours. This activity significantly exceeds that of the long acting drug Octreotide, which has a circulation half-life of only 40 minutes. The main pharmacokinetic parameters of PTR 3173 vs. Octreotide are summarised in table 5.

found by screening both analogs and SRIF for binding to several such receptors (example 6). This characteristic is of great advantageous because binding to non-somatostatin receptors could cause potential adverse effects in the body.

PTR 3173 was furthermore found to be not mitogenic for human lymphocytes in human peripheral blood lymphocytes (PBL) proliferation assays.

PTR 3113 and PTR 3123 were found to be safe when administered intravenously to rats in a single dose of 6 mg/kg. PTR 3173 was tested in various species for its initial safety properties. Under the European Pharmacopoeia requirements for safety testing, it was declared a safe drug candidate at this stage of development. No toxicity signs in rodents or in dogs were seen when injected at a dose 10,000-fold higher then the efficacious dose for inhibiting Growth hormone release.

General Method for Synthesis, Purification and Characterization of Backbone Cyclic Peptides Synthesis:

Resin:

1 g Rink amide or Tenta-gel resin, with loading of 0.2–0.7 mmol/g.

Fmoc-deprotection:

With 7 mL of 20% piperidine in NMP. Twice for 15 minutes following 5 washes with 10 mL NMP for 2 minutes with shaking.

Couplings:

1. Regular couplings (coupling to simple amino acids): with a solution containing 3 equivalents amino acid, 3 equivalents PyBroP and 6 equivalents of DIEA in 7 mL NMP. For 0.5–2 hours with shaking. Coupling is monitored by ninhydrine test and repeated until the ninhydrine solution become yellow.

2. Coupling of His and Asn with a solution containing 5 equivalents DIC and 5 equivalents HOBT in 10 mL DMF.

3. Coupling to Gly building units: with a solution containing 3 equivalents amino acid, 3 equivalents PyBroP and 6 equivalents DIEA in 7 mL NMP. Twice for 1–4 hours with shaking.

4. Coupling to building units which are not Gly: with a solution containing 5 equivalents amino acid, 1.5 equivalents triphosgene and 13 equivalents collidine in 15 mL dioxane or THF. Twice for 0.5–2 hours at 50° C. with shaking.

Removal of the Allyl and Alloc Protecting Groups of the Building Units:

With 1.5 equivalents per peptide of $Pd(PPh3)_4$ in 30 mL DCM containing 5% acetic acid and 2.5% NMM. For 1–4 hours with shaking.

Cyclization:

With a solution containing 3 equivalents PyBOP and 6 equivalents DIEA in 7 mL NMP. For 0.5–2 hours with shaking. Cyclization is monitored by ninhydrine test and repeated if necessary.

Cleavage:

With 82%–95% TFA supplemented with scavengers: 1–15% $H_2O$, 1–5% TIS and 1–5% EDT.

Purification:

An individual purification method for each backbone cyclic peptide is developed on analytical HPLC to give the maximum isolation of the cyclic peptide from other crude components. The analytical method is usually performed using a C-18 Vydac column 250×4.6 mm as the stationary phase and water/ACN containing 0.1% TFA mixture gradient.

The preparative method is designed by implying the analytical separation method on the 2" C-18 Vydac preparative method. During the purification process, the peak containing the cyclic peptide is collected using a semi-automated fraction collector. The collected fractions are injected to the analytical HPLC for purity check. The pure fractions are combined and lyophilized.

Characterization:

The combined pure lyophilized material is analyzed for purity by HPLC, MS and capillary electrophoresis and by amino acid analysis for peptide content and amino acid ratio determination.

Preparation of Peptides with Backbone to Side Chain Cyclization.

One preferred procedure for preparing the desired backbone cyclic peptides involves the stepwise synthesis of the linear peptides on a solid support and the backbone cyclization of the peptide either on the solid support or after removal from the support. The C-terminal amino acid is bound covalently to an insoluble polymeric support by a carboxylic acid ester or other linkages such as amides. An example of such support is a polystyrene-co-divinyl benzene resin. The polymeric supports used are those compatible with such chemistries as Fmoc and Boc and include for example PAM resin, HMP resin and chloromethylated resin. The resin bound amino acid is deprotected for example with TFA and to it is coupled the second amino acid, protected on the $N^\alpha$ for example by Fmoc, using a coupling reagent like BOP. The second amino acid is deprotected using for example piperidine 20% in DMF. The subsequent protected amino acids can then be coupled and deprotected at ambient temperature. After several cycles of coupling and deprotection that gives peptide, an amino acid having for example carboxy side chain is coupled to the desired peptide. One such amino acid is Fmoc-aspartic acid t-butyl ester. After deprotection of the $N^\alpha$ Fmoc protecting group, the peptide is again elongated by methods well known in the art. After deprotection a building unit for backbone cyclization is coupled to the peptide resin using for example the coupling reagent BOP. One such building unit is for example Fmoc-$N^\alpha$-ω-Boc-amino alkylene)amino acid. After deprotection the peptide can then be elongated, to the desired length using methods well known in the art. The coupling of the protected amino acid subsequent to the building unit is performed by such coupling agents exemplified by PyBrOP to ensure high yield.

After the linear, resin bound peptide, has been prepared the co-alkylene-protecting groups, for example Boc and t-Bu, are removed by mild acid such as TFA.

The resin bound peptide is then divided into several parts. One part is subjected to on-resin cyclization using for example TBTU as cyclization agent in DMF to ensure high yield of cyclization, to give the N-backbone to side chain cyclic peptide resin. After cyclization on the resin the terminal amino protecting group is removed by agents such as piperidine and the backbone to side chain cyclic peptide is obtained after treatment with strong acid such as HF. Alternatively, prior to the removal of the backbone cyclic peptide from the resin, the terminal amino group is blocked by acylation with agents such as acetic anhydride, benzoic anhydride or any other acid such as adamantyl carboxylic acid activated by coupling agents such as BOP.

The other part of the peptide-resin undergoes protecting of the side chains used for cyclization, for example the ω-amino and carboxy groups. This is done by reacting the ω-amino group with for example $Ac_2O$ and DMAP in DMF and activating the free ω-carboxy group by, for example, DIC and HOBT to give the active ester which is then reacted with, for example, $CH_3NH_2$ to give the non-cyclic analog of the cyclic peptide. Removal of the peptide from the resin and subsequent removal of the side chains protecting groups by strong acid such as HF to gives the non-cyclic analog of the backbone to side chain cyclic peptide.

The linear and/or non-cyclic analogs are used as reference compounds for the biological activity of their corresponding cyclic compounds.

General Screening of Somatostatin Analogs.

The backbone cyclic somatostatin analogs are screened by testing them in-vitro for their inhibition of the natural peptide (SRIF-14) binding to its G-protein coupled receptors (example 3). Analogs which bind with high affinity are then tested for their influence on second messengers such as cyclic adenosine monophosphate (cAMP) levels, tyrosine phosphatase activity, growth hormone and chromogranin A secretion, and on cell growth.

Active analogs are furthermore tested in-vivo for inhibition of hormones and enzyme secretion particular relevant model systems based on literature data indicating that SST-R2 and SST-R5 mediate most endocrine effects of Somatostatin, are inhibition of growth-hormone release, and amylase, gastric acid, insulin and glucagon secretion which are based on the known endocrine activities of the native hormone SRIF and the somatostatin analog, Octreotide.

The most preferred backbone cyclic somatostatin analogs: PTR-3201, PTR-3205 and PTR-3173, which possess receptor specificity to SST-R5, SST-R2 and SST-R2+SST-R5 respectively, were used to elucidate the physiological role of each somatostatin receptor on the endocrine profiles in addition to finding their potentials as drug candidates.

Conformationally constrained somatostatin analogs constructed based in part on the sequences of a number of known biologically active peptides or based on previously unknown novel sequences are presented in the examples below. The following examples are intended to illustrate how to make and use the compounds and methods of this invention and are in no way to be construed as a limitation.

EXAMPLES

Example 1
Detailed Synthesis of SST PTR 3173 Analog

Five grams of Rink amide resin (NOVA) (0.56 mmol/g), were swelled in N-methylpyrrolidone (NMP) in a reaction vessel equipped with a sintered glass bottom and placed on a shaker. The Fmoc protecting group was removed from the resin by reaction with 20% piperidine in NMP (2 times 10 minutes, 25 mL each). Fmoc removal was monitored by ultraviolet absorption measurement at 290 nm. A coupling cycle was carried out with Fmoc-Gly-C3(Allyl) (3 equivalents) PyBrop (3 equivalents) DIEA (6 equivalents) in NMP (20 mL) for 1 hour at room temperature. Reaction completion was monitored by the qualitative ninhydrin test (Kaiser test).

Following coupling, the peptide-resin was washed with NMP (7 times with 25 mL NMP, 2 minutes each). Capping was carried out by reaction of the peptide-resin with acetic anhydride (capping mixture: HOBt 400 mg, NMP 20 mL, acetic anhydride 10 mL, DIEA 4.4 mL) for 0.5 hours at room temperature. After capping, NMP washes were carried out as above (7 times, 2 minutes each). Fmoc removal was carried out as above. Fmoc-Phe-OH was coupled in the same manner, and the Fmoc group removed, as above. The peptide resin was reacted with Fmoc-Thr(OtBu)-OH: coupling conditions were as above. Fmoc removal was carried out as above. Fmoc-Lys(Boc)-OH was coupled to the peptide resin by the same coupling conditions. Coupling completion was monitored by the Fmoc test (a sample of the peptide resin was taken and weighed, the Fmoc was removed as above, and the ultraviolet absorption was measured). Fmoc-D-Trp-OH was coupled to the peptide resin with PyBrop, as described above. Following Fmoc removal, Fmoc-Trp-OH was coupled in the same way. Following Fmoc removal, Fmoc-Phe-OH was coupled in the same manner. Following Fmoc removal, Fmoc-GABA-OH was coupled in the same way.

The Allyl protecting group was removed by reaction with Pd(PPh$_3$)$_4$ and acetic acid 5%, morpholine 2.5% in chloroform, under argon, for 2 hours at room temperature. The peptide resin was washed with NMP as above. The Fmoc protecting group was removed from the peptide by reaction with 20% piperidine in NMP (2 times 10 minutes, 25 mL each). Cyclization was carried out with PyBOP 3 equivalents, DIEA 6 equivalents, in NMP, at room temperature for 2 h. The peptide resin was washed and dried. The peptide was cleaved from the resin by reaction with TFA 94%, water 2.5%, EDT 2.5%, TIS (tri-isopropyl-silane) 1%, at 0° C. for 15 minutes and 2 hours at room temperature under argon. The mixture was filtered into cold ether (30 mL, 0° C.) and the resin was washed with a small volume of TFA. The filtrate was placed in a rotary evaporator and all the volatile components were removed. An oily product was obtained. It was triturated with ether and the ether decanted, three times. A white powder was obtained. This crude product was dried. The weight of the crude product was 4 g.

After purification by HPLC a signal peak was obtained with 100% purity as detected by analytical HPLC and capillary electrophoresis. The expected mass of 1123 daltons was detected by mass spectroscopy.

Example 2
Detailed Procedure of PTR 3205 Synthesis by the Triphosgen Method.

Two grams of Rink Amide (MBHA resin, NOVA, 0.46 mmol/gr) were swelled over night in NMP in a reactor equipped with a sintered glass bottom, attached to a shaker. Fmoc was removed from the resin using 25% Piperidine in NMP (16 ml) twice for 15 min. After careful wash, seven times with NMP (10–15 ml), for 2 min. each, coupling of Phe-N3 was accomplished using Fmoc-Phe-N3-OH (3 eq, 2.76 mmol, 1.46 g') dissolved in NMP (16 ml) and activated with PyBroP (2.76 mmol, 1.28 g') and DIEA (6eq, 5.52 mmol, 0.95 ml) for 4 min at room temperature and then transferred to the reactor for coupling for 1 h at room temperature. Following coupling the peptide-resin was washed with NMP (10–15 ml) seven times for 2 min each. Reaction completion was monitored by qualitative Ninhydrine test (Kaiser test). Fmoc removal and wash was carried out as described above followed by wash with THF (10–15 ml) three times for 2 min each and Fmoc-Cys(Acm)-OH (5 eq, 4.6 mmol, 1.9 g') was coupled to the BU-peptidyl-resin using bis-(trichloromethyl) carbonate (1.65 eq, 1.518 mmol, 0.45 g') and collidine (14 eq, 12.88 mmol, 1.7 ml) in THF (30–35 ml, to give 0.14 M mixture) at 50° C. for 1 h. and this coupling procedure was repeated. Assembly of Thr, Lys, (D)Trp, Phe, Cys and PheC3 was accomplished by coupling cycles (monitored by qualitative Ninhydrine test) using Fmoc-Thr(tBu)-OH, Fmoc-Lys(Boc)-OH, Fmoc-(D)Trp(Boc)-OH, Fmoc-Phe-OH, Fmoc-Cys(Acm)-OH and Fmoc-PheC3-OH respectiviely, in each coupling cycle the amino acid was dissolved in NMP and was activated with PyBroP and DIEA, following coupling the peptide-resin was washed than Fmoc removed followed by extensive wash with NMP, as described above for the first coupling. At the end of the assembly the peptidyl-resin underwent allyl/alloc deprotection under the following conditions: the peptidyl resin was washed with DCM (10–15 ml) three times for 2 min each and with a mixture of DCM-AcOH-NMM (92.5%, 5%, 2.5% respectively) three times for 2 min each. 3 g' of Pd(P(Ph)$_3$)$_4$ were dissolved in the above mixture (80 ml) and the yellow suspension obtained was transferred to the reactor and the mixture with the peptidyl-resin underwent degassing (by babbling Argon through the reactor's sintered glass bottom) and then vigorously shacked for 2 h. in the dark. The peptidyl-resin washed with DCM, CHCl$_3$ and NMP (a total of 15 washes 2 min each). Cyclization using PyBOP (3eq, 2.76 mmol, 1.436 g') and DIEA (6 eq, 5.52 mmol, 0.95 ml) in NMP (20 ml) at rt. for 1 h. and then second cyclization over night (under same conditions) took place. The peptidyl resin was washed with NMP followed by wash with DMF-water (15 ml, 4:1) three times for 2 min. each. I$_2$ solution (5 eq, 4.6 mmol, 1.16 g') in DMF-water (23 ml, 4:1) was added to the peptidyl-resin which was shacked at rt. for 40 min. to afford Cys-Cys cyclization. The peptidyl resin was filtered and washed extensively with DMF/water, DMF, NMP, DCM, CHCl$_3$ and also with 2% ascorbic acid in DMF. After final Fmoc deprotection and wash as above and also wash with MeOH, followed by drying the peptidyl resin under vacuum for 20 min. the peptide was cleaved from the resin using 95% TFA, 2.5% TIS and 2.5% water in a total of 30 ml cocktail mixture for 30 min. at 0° C. under Argon and then 1.5 h. at rt. The solution was filtered through extract filter into polypropylene tube, the resin was washed with 5–6 ml cocktail and 4–5 ml TFA, the solution was evaporated by N$_2$ stream to give oily residue which on treatment with cold Et$_2$O solidify. Centrifugation and decantation of the Et$_2$O layer and treatment with additional portion of cold Et$_2$O followed by centrifugation and decantation and drying the white solid under vacuum over night gave crude PTR-3205-02 (0.388 g', 30%).

Example 3
Resistance to Biodegradation

The in vitro biostability of SST cyclic peptide analogs; PTRs 3113, 3123, and 3171, was measured in renal homogenate, and were compared to Octreotide (SandostatinÔ), and to native somatostatin (SRIF-14). The results are shown in the Table 4 below. In this assay, the backbone cyclic peptide analogs of the present invention were as stable as Octreotide, and were much more stable than SRIF. The assay was based on HPLC determination of peptide degradation as a function of time in renal homogenate at 37° C.

TABLE 4

Percent of intact molecule after incubation in renal homogenate.

| Time (hrs) | SRIF | Octreotide | PTR-3113 | PTR-3123 | PTR-3171 | PTR-3173 |
|---|---|---|---|---|---|---|
| 0 | 100 | 100 | 100 | 100 | 100 | 100 |
| 1 | 5 | 100 | 100 | 100 | 100 | 100 |
| 3 | 0 | 100 | 100 | 100 | 100 | 100 |
| 24 | 0 | 100 | 100 | 100 | 100 | 100 |

Example 4
Binding of Analogs to Somatostatin Receptors

The somatostatin analogs were tested for their potency in inhibition of the binding of $^{125}$I-Tyr$^{11}$-SRIF (based on the method described by Raynor et. al., *Molecular Pharmacology*, 1993, 43, 838–844) to membrane preparations expressing the transmembranal somatostatin receptors (SSTR-1, 2, 3, 4 or 5). The receptor preparations used for these tests were either from the cloned human receptors selectively and stably expressed in Chinese Hamster Ovary (CHO) cells or from cell lines naturally expressing the SSTRs. Typically, cell membranes were homogenated in Tris buffer in the presence of protease inhibitors and incubated for 30–40 minutes with $^{125}$I-Tyr$^{11}$-SRIF with different concentrations of the tested sample. The binding reactions were filtered, the filters were washed and the bound radioactivity was counted in gamma counter. Non specific binding was defined as the radioactivity remaining bound in the presence of 1 μM unlabeled SRIF-14.

In order to validate positive signals of the binding tests, and to eliminate non-specific signals, samples of irrelevant peptides, such as GnRH, that were synthesized and handled using the same procedures, were tested in the same assays as negative control samples. These samples had no binding activity in any of the assays. Results are shown below in Tables 5 and 6 and FIG. 1.

TABLE 7

Percent inhibition of SRIF-14 binding to cloned human somatostatin receptors 3 and 5 by backbone cyclic analogs.

| | SST-R3 | | | SST-R5 | | |
|---|---|---|---|---|---|---|
| Concentration | 10$^{-8}$M | 10$^{-7}$M | 10$^{-6}$M | 10$^{-8}$M | 10$^{-7}$M | 10$^{-6}$M |
| PTR-3113 | 16 | 65 | 94 | 0 | 50 | 86 |
| PTR-3123 | 24 | 41 | 84 | 0 | 0 | 0 |
| PTR-3171 | 12 | 40 | 87 | 18 | 10 | 60 |

TABLE 7-continued

Percent inhibition of SRIF-14 binding to cloned human somatostatin receptors 3 and 5 by backbone cyclic analogs.

| | SST-R3 | | | SST-R5 | | |
|---|---|---|---|---|---|---|
| Concentration | 10$^{-8}$M | 10$^{-7}$M | 10$^{-6}$M | 10$^{-8}$M | 10$^{-7}$M | 10$^{-6}$M |
| Total counts | | 12000 CPM | | | 3600 CPM | |
| Non-specific binding | | 1200 CPM | | | 900 CPM | |
| blank | | 400 CPM | | | 400 CPM | |

TABLE 8

Percent inhibition of SRIF-14 binding to cloned human somatostatin receptors by PTR 3173.

| | Concentration (M) | | | | | |
|---|---|---|---|---|---|---|
| Receptor Subtype | 10$^{-11}$ | 10$^{-10}$ | 10$^{-9}$ | 10$^{-8}$ | 10$^{-7}$ | 10$^{-6}$ |
| SSTR-R1 | 0 | 0 | 0 | 0 | 5 | 15 |
| SSTR-R2 | 15 | 30 | 42 | 80 | 95 | 96 |
| SSTR-R3 | 2 | 1 | 1 | 4 | 50 | 89 |
| SSTR-R4 | 0 | 0 | 0 | 0 | 5 | 5 |
| SSTR-R5 | 20 | 48 | 63 | 82 | 95 | 95 |

Example 5
Binding of Additional Analogs to Somatostain Receptors

Method is as in example no. 3. Results are shown in table 9 below.

TABLE 9

Concentration (nM) of somatostain analogs to inhibit SRIF binding to each human cloned somatostatin receptors SSTR-n) by 50%.

| | IC 50 (nM) | | | |
|---|---|---|---|---|
| PTR | SSTR-1 | SSTR-2 | SSTR-3 | SSTR-5 |
| 3201 | >10$^{-6}$ | 10$^{-7}$ | 10$^{-8}$ | 10$^{-9}$ |
| 3203 | >10$^{-7}$ | 10$^{-7}$ | 10$^{-8}$ | 10$^{-8}$ |
| 3197 | 10$^{-8}$ | 10$^{-8}$ | 10$^{-9}$ | 10$^{-8}$ |
| 3205 | >10$^{-6}$ | 10$^{-9}$ | >10$^{-6}$ | >10$^{-6}$ |
| 3207 | 10$^{-7}$ | 10$^{-9}$ | 10$^{-9}$ | 10$^{-8}$ |
| 3173 | >10$^{-6}$ | 10$^{-9}$ | 10$^{-7}$ | 10$^{-9}$ |

Example 6
In-vitro Bio-response of Preferred Backbone Cyclic Somatostatin Analogs.
A. Inhibition of cAMP in Human Carcinoid BON-1 Cells by the Backbone Cyclic Somatostatin Analog PTR 3173:

The activation of SST-R5 leads to the reduction of Adenylate Cyclase activity. Somatostatin receptors including type-5 receptors are expressed in the human Carcinoid derived cell line BON-1. This human cell culture served as an in-vitro discovery assay for novel Carcinoid therapeutics. Interaction of somatostatin analogs with Somatostatin receptors expressed in this system subsequently affects cellular functionality of BON-1. It was found that preferred backbone cyclic analogs of the present invention inhibit cAMP production following Forskolin stimulation. In this signal transudation pathway PTR 3173 is equipotent to clinically used drug Octreotide.

B. In-vitro Cell-growth Inhibition by the Backbone Cyclic Somatostatin Analog PTR 3173:

Pharmacological evaluation of growth inhibition was performed utilizing CHO cells expressing human cloned SST-R5. PTR 3173 recognition of SST-R5 at the cellular level was associated with considerably higher potency of growth inhibition compared to the native hormone and the drug Octreotide.

C. Inhibition of Chromogranin A Release by the Backbone Cyclic Somatostatin Analog PTR 3137:

Assessment of Chromogranin A release from BON-1 is an important assay aimed at identifying potential anti Carcinoid drugs. Chromagranin A is one of the principal mediators in degranulation of tumor granules, which secrete excessive amounts of vasoactive substances from Carcinoid tumors. PTR 3173 possesses a significant anti-release effect on this pathway. One of the most intriguing findings of the backbone cyclic analog in the human BON-1 assay, is its equivalent potency with the native hormone Somatostatin, indicating a potential beneficial effect on Carcinoid syndrome.

Example 7

Comparison of PTR 3173, Octreotide and SRIF for Binding to Non-somatostatin G-coupled Receptors.

Somatostatin receptors belong to the seven transmembrane G-protein coupled receptors super family. G-protein coupled receptors are widely distributed in the body and mediate physiological activities of various hormones such as Adrenaline, Acetylcholine, Opiates, Neurokinins, Gastrin, and many other hormones. A drug candidate could be recognized by defined subtype of intra family receptors. However, it could cause potential adverse effects in the body due to recognition of other receptors distinct from its family. This consideration raised the importance of inter-versus intra-receptor selectivity, in the context of developing physiological selective drugs.

Figure 2:
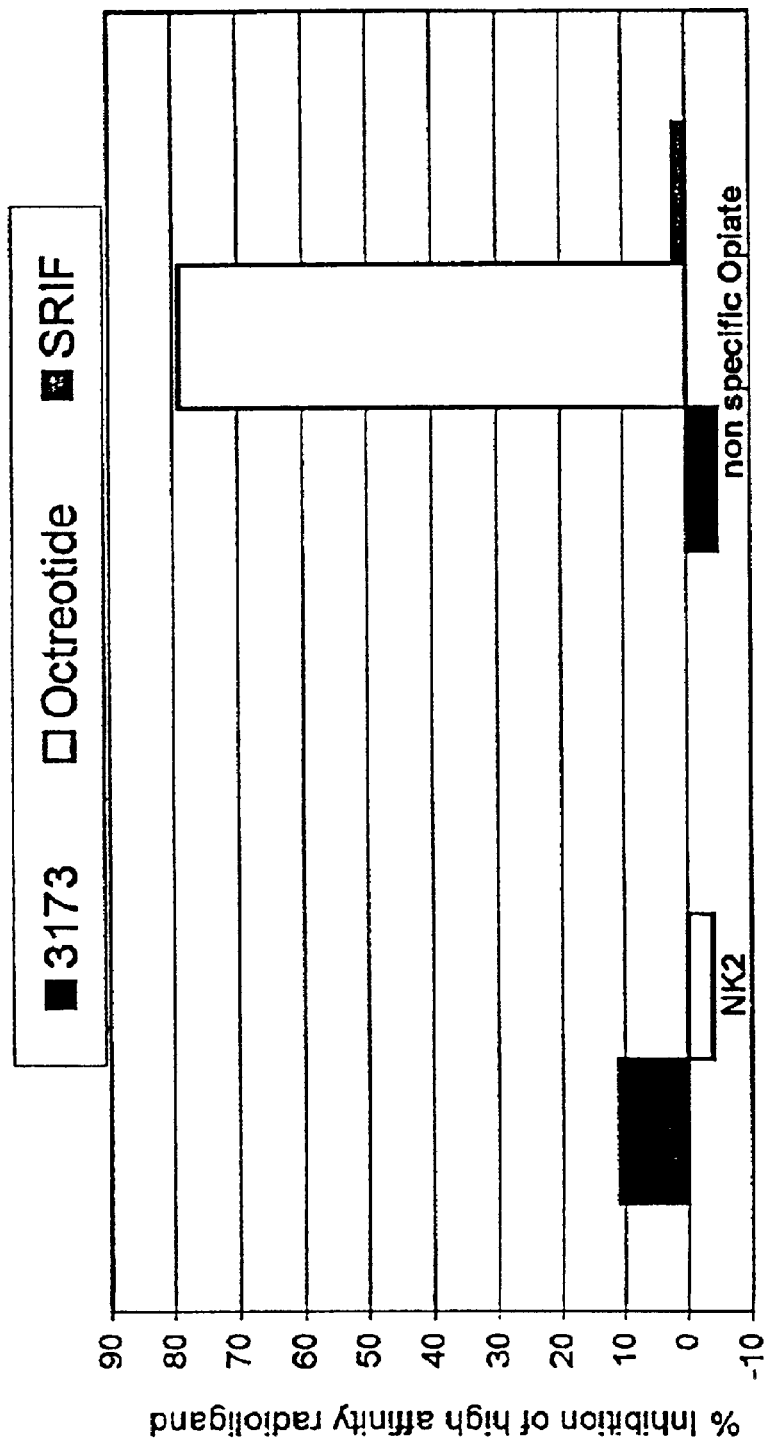
FIG. 2 is a graph showing the non-specific binding of Somatostatin analogs (tested at a concentration of 100 nM) to various G-Protein coupled receptors.

NovaScreen (Hanover, Md.) performed an assessment for nonspecific binding to various G-protein coupled receptor families. Binding studies to Neurokinin, Opiate and Muscarinic receptors were based on a comparison between the native hormone Somatostatin, Ocreotide and PTR 3173. In a screening assay performed by Novascreen, significant high affinity of Octreotide to Opiate receptors was found, while under the same experimental conditions PTR 3173 and the native hormone Somatostatin did not bind to these receptors (FIG. 2). Significant higher affinity of Octreotide above PTR 3173 and the native hormone was also found to the Muscarinic-2 receptor.

The significance of cross reactive binding of Octreotide to the Opiate receptors was further investigated in the Guinea-Pig Ileum. Preliminary results confirm the effect of Octreotide as an Opiate antagonist, while under the same experimental conditions PTR 3173 did not affect met-Enkephalin-evoked twitch contraction.

Example 8

In in-vivo Effect of Receptor-specific Backbone Cyclic Somatostatin Analogs on Growth Hormone Release.

Methods:

Inhibition of growth hormone (GH) release as a result of peptide administration was measured in Wistar male rats. The analog activity was compared in this study to SRIF or to Octreotide using 4 rats in each group.

Figure 3:
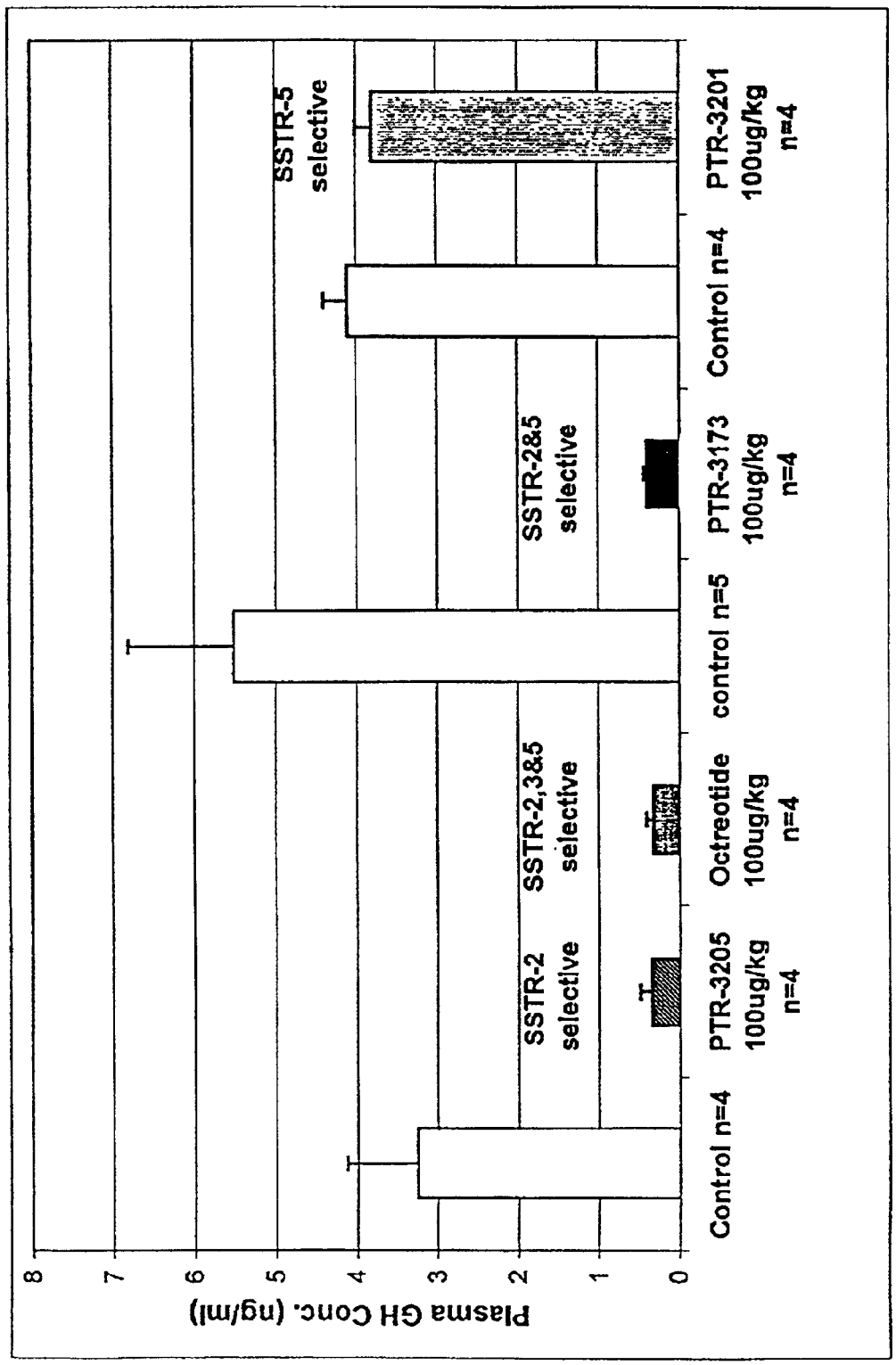
FIG. 3 is a graph showing the effect of somatostatin analog according to the present invention on the release of growth hormone compared to Octreotide.

Adult male Wistar rats weighing 200–250 g, were maintained on a constant light-dark cycle (light from 8:00 to 20:00 h), temperature (21±3° C.), and relative humidity (55±10%). Laboratory chow and tap water were available ad libitum. On the day of the experiment, rats were anesthetized with Nembutal (IP, 60 mg/kg). Ten minutes after anesthesia, drugs were administered S.C. at 0.01–100 microgram/kg dose. Stimulation of GH was performed by I.V. administration of 0.5 g/kg of L-Arginine through femoral vein. Sampling was carried out following 5 minutes of stimulation, at 15 or 30 minutes after peptide administration. Blood samples were collected form abdominal vena-cava into tubes containing heparin (15 units per ml of blood) and centrifuged immediately. Plasma was separated and kept frozen at −20° C. until assayed. Rat growth hormone (rGH) [$^{125}$I] levels were determined by means of a radioimmunoassay kit (Amersham). The standard in this kit has been calibrated against a reference standard preparation (NIH-RP2) obtained from the National Institute of Diabetes and Digestive and Kidney Diseases. All samples were measured in duplicate. The results of these experiments are shown in FIG. 3.

Results:

Growth hormone release was stimulated in rats using intravenous (IV) bolus administration of L-arginine under Nembutal anesthesia. The reported ED50 for Octreotide (Bauer, et al. ibid.) in this model is approximately 0.1 micrograms per kilogram. Consequently, Octreotide and the tested receptor-specific backbone cyclic analogs were administered at a relatively high dose of 100 micrograms per kilogram. Under these experimental conditions PTR-3205 and PTR 3173 were equipotent inhibitors of growth hormone release in comparison to Octreotide (FIG. 3). Intriguing results were found with PTR-3201, which is a receptor 5 specific analog. This selective analog did not affect growth hormone release thus demonstrating that growth hormone inhibition is not mediated by somatostatin receptor subtype 5. On the other hand, the significant inhibition found with PTR-3205, which is s selective to receptor subtype 2, indicate that this is the principal receptor, which mediates growth hormone inhibition. Therefore, we can deduce that the effect on growth hormone found with the drug Octreotide or PTR 3173 is due to their recognition of receptor subtype 2.

Additional results of GH inhibition by PTR 3132 compare to Octreotide are described in table 10.

TABLE 10

| | Plasma growth hormone concentration (ng/ml) | | | |
|---|---|---|---|---|
| | Control | None | Octreotide | PTR-3123 |
| | 1.03 | | 0.48 | 10 |
| | 10 | 0.46 | 0.56 | 6.37 |
| | 10 | 2.7 | 0.46 | 7.4 |
| | 10 | 4.54 | 0.43 | 10 |
| | 10 | | 0.43 | 10 |
| | 10 | | 0.61 | 10 |
| Average | 8.72 | 2.33 | 0.50 | 8.96 |
| SE | 1.28 | 0.87 | 0.03 | 0.67 |

Example 9
The in-vivo Effect of Receptor-specific Backbone Cyclic Somatostatin Analogs on Glucagon Release.

In-vivo determination of the release of glucogon as a result of peptide administration was measured in Wistar male rats.

The analog activity was compared in this study to SRIF or to Octreotide using 4 rats in each group. Time course profiles for glucagon release under constant experimental conditions were measured.

Male Wistar rats were fasted overnight. Animals were anesthetized with Nembutal (IP, 60 mg/kg). Ten minutes after anesthesia, drugs were administrated S.C. at 0.01–100 microgram/kg dose. Stimulation of glucagon secretion was performed by I.V. administration of L-arginine, 0.5 g/kg, 5 minutes before blood collection from portal vein. Hormone concentration was measured by RIA.

Figure 4:
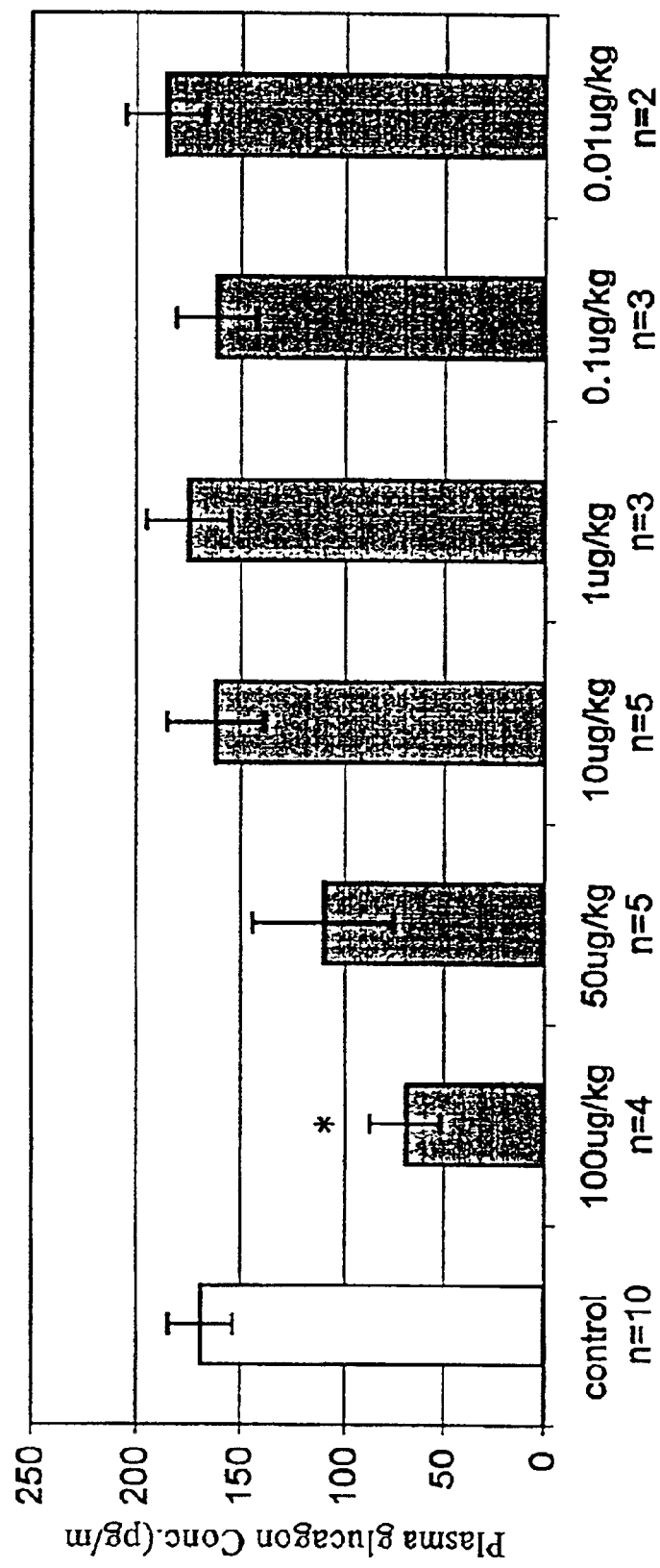
FIG. 4 is a graph showing the dose response effect of the somatostatin analog according to the present invention on the release of glucagon.

The only statistically significant difference in glucagon levels compare to control was obtained with the high dose of 100 micrograms per kilogram of PTR 3173 (FIG. 4), a 1000 fold higher dose in comparison to the Ed50 of PTR 3173 on growth hormone release. These results emphasize this backbone cyclic analog significant physiological selectivity compared to Octreotide as summarized in Table 4 above.

Additional results of glucogon inhibition by PTR 3132 compare to Octreotide are described in table 11.

TABLE 11

Plasma glucagon concentration (ng/ml)

|  | Control | None | Octreotide | PTR-3123 |
|---|---|---|---|---|
|  | 189 | 18 | 20 | 58 |
|  | 76 | 9.5 | 89 | 52 |
|  | 145 | 32 | 62 | 20 |
|  | 37 | 20 | 70 | 84 |
|  | 131 |  | 37 | 87 |
|  | 44 |  | 20 | 20 |
|  | 67 |  |  |  |
| Average | 98.4 | 19.9 | 49.7 | 53.5 |
| SE | 21.6 | 4.6 | 11.6 | 12.0 |

Example 10
The in-vivo Effect of Receptor-specific Backbone Cyclic Somatostatin Analogs on Insulin Release.

The inhibition of insulin release by Somatostatin analogs is well documented in the literature (Bauer, et al. ibid., Lamberts et al. 1996, ibid.). However, synthetic Somatostatin analogs with a long duration of physiological activity were reported to be less active on insulin in comparison to their potent inhibition of growth hormone or glucagon release (Bauer, et al. ibid., Lamberts et al. 1996, ibid.). Sandoz claims that there is physiological selectivity of Octreotide on growth hormone versus insulin. However, in Type 2 diabetes the long acting analog Octreotide suppresses of insulin and glucagon release, leaving glucose levels either unchanged or somewhat elevated.

Other clinical trials have shown that the failure of Octreotide to diminish glycemic values in Type 2 diabetes in spite of its ability to lower glucagon and growth hormone was probably dependent on temporary blockade of residual endogenous insulin secretion induced by its administration. In healthy subjects the administration of Octreotide resulted in the development of mild fasting hyperglycemia and marked fasting hypoinsulinemia. Furthermore, Octreotide is prescribed for the treatment of nesidioblastosis, a syndrome associated with excessive release of insulin from the pancreas, which emphasizes Octreotide's physiological non-specific effect on insulin (Kane et al. J. Clin. Inves. 100:1888, 1997).

In order to evaluate the physiological effects of receptor specific backbone cyclic somatostatin analogs on insulin release, the same experimental protocol used by Sandoz for the evaluation of Octreotide was performed. Insulin stimulation was induced by IV bolus administration of D-glucose to overnight fasted rats.

Method:

An in-vivo determination of insulin release as a result of peptide administration was measured in Wistar male rats. The analog activity was compared in this study to SRIF or to Octreotide using 4 rats in each group. Time course profiles for GH release under constant experimental conditions were measured.

Male Wistar rats were fasted overnight. Animals were anesthetized with Nembutal (IP, 60 mg/kg). Ten minutes after anesthesia, drugs were administrated S.C. at 0.01–100 microgram/kg dose 30 minutes before stimulation of insulin secretion performed by I.V. administration of 0.5 g/kg of D-glucose, 5 minutes before blood collection from abdominal Vena-cava. Hormone levels wer measured by RIA.

Figure 5:
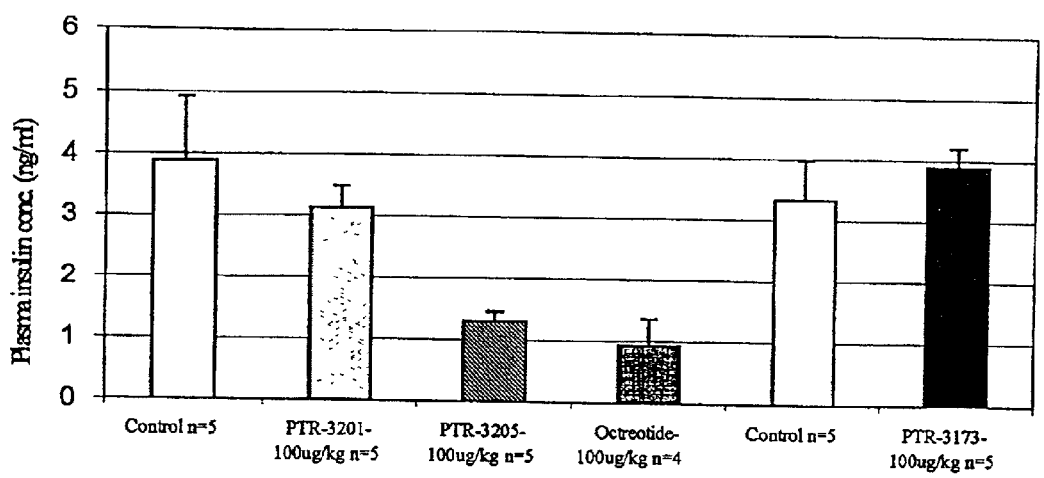
FIGS. 5a and 5b are graphs showing the effect of somatostatin analogs according to the present invention on the release of insulin compared to Octreotide in three distinct experiments.
Figure 5:
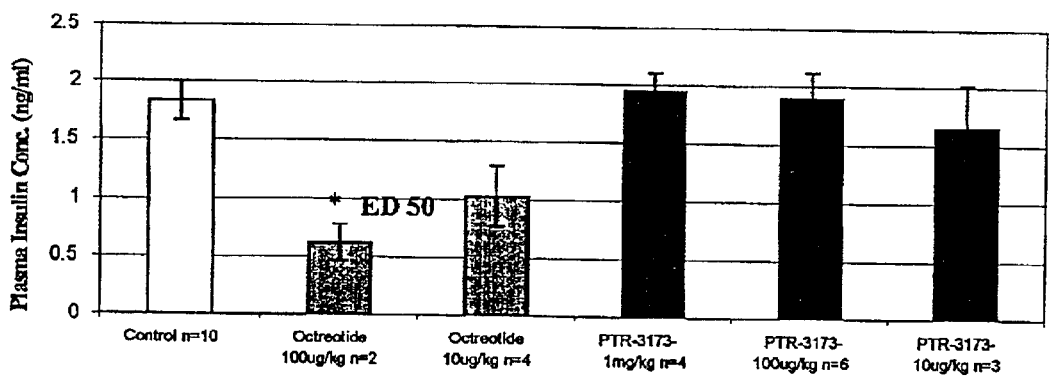

Results:

PTR-3205 and Octreotide were both active inhibitors of insulin release (FIG. 5a). The ED50 of Octreotide following subcutaneous injection was between 10 to 100 micrograms per kilogram, in accordance with the ED50 reported by Sandoz—26 micrograms per kilogram. The significant effect found with PTR-3205, indicates that Somatostatin receptor subtype 2 mediates the effect on growth hormone and also on insulin. This receptor-effector relationship was correlated with previous published data which indicated that somatostatin inhibits β-cell secretion via receptor subtype 2 in the isolated perfused human pancreas. In contrast to the significant effect found PTR-3205 and Octreotide, high doses (100 micrograms per kilogram) of PTR-3201 and PTR 3173—were inactive on insulin. It should be noted that to PTR 3173 in a similar dose had a significant effect on the release of growth hormone. This intriguing physiological selectivity of PTR 3173 led us to repeat this experiment with a much higher dose of up to 1 milligram per kilogram. Under these experimental conditions, PTR 3173 was defined as a physiologically selective Somatostatin analog with no appreciable effect on insulin in comparison to the drug Octreotide (FIG. 5b).

Additional results of glucagon inhibition by PTR 3132 compare to Octreotide are described in table 12.

TABLE 12

Plasma insulin concentration (ng/ml)

| Control | None | Octreotide | PTR-3123 |
|---|---|---|---|
| 3.97 | 1 | 3.5 | 1.46 |
| 4.14 | 2.5 | 1.95 | 5.66 |
| 5.12 | 0.7 | 3.7 |  |
| 3.8 | 0.74 | 3.06 | 2.44 |
| 2.7 |  | 2 | 1.87 |
| 3 |  | 1.1 | 2.8 |
| 1.5 |  |  |  |

TABLE 12-continued

| | Plasma insulin concentration (ng/ml) | | | |
|---|---|---|---|---|
| | Control | None | Octreotide | PTR-3123 |
| Average | 3.46 | 1.24 | 2.55 | 2.85 |
| SE | 0.44 | 0.43 | 0.42 | 0.74 |

Example 11
Additional Preferred Backbone Cyclic Somatostatin Analogs.

Additional preferred somatostatin analogs that were synthesized are described in tables 13 and 14.

TABLE 13

Additional somatostatin analogs.

| PTR No. | Sequence |
|---|---|
| 3102 | NMeAla-Tyr-(D)Trp-Lys-Val-Phe(C3)-NH2 |
| 3135 | (D)Phe-Phe-Phe(N2)-(D)Trp-Lys-Thr-Phe(C3)-Thr-NH2 |
| 3137 | (D)Phe(N2)-Phe-Phe(C3)-(D)Trp-Lys-Thr-Phe-Thr-NH2 |
| 3139 | H-(D)Phe-Ala(N3)-Phe-(D)Trp-Lys-Phe-Ala(C3)-Thr-NH2 |
| 3141 | (D)Nal-Gly(S2)*-Tyr-(D)Trp-Lys-Val-Cys*-Thr-NH2 |
| 3143 | Phe(C1)-Phe-(D)Trp-Lys-(D)Thr-Phe(N2)-NH2 |
| 3145 | Phe-Phe-His-(D)Trp-Lys-Thr-Phe(C3)-Thr-NH2 |
| 3147 | Ala-Phe-His-(D)Trp-Lys-Thr-Phe(C3)-Thr-NH2 |
| 3153 | (D)Ala-Phe-His-(D)Trp-Lys-Thr-Phe(C3)-Thr-NH2 |
| 3155 | (D)Phe-Phe-His-(D)Trp-Lys-Thr-PheC3)-Thr-NH2 |
| 3157 | Aib-Phe-His-(D)Trp-Lys-Thr-Phe(C3)-Thr-NH2 |
| 3159 | Fmoc-Gly(S1)-Phe-(D)Trp-Lys-Thr-Cys-Thr-OL |
| 3161 | (D)Phe-Orn*-Phe-(D)Trp-Lys-Thr-Phe(C3)-Thr-OL |
| 3163 | (D)Phe-Phe(C3)-Phe-(D)Trp-Lys-Thr-DAP*-Thr-OL |
| 3165 | (D)Phe-Phe(C3)-Phe-(D)Trp-Lys-Thr-Lys*-Thr-OL |
| 3187 | Phe(C1)-Phe-Leu-(D)Trp-(D)Lys-Phe(N2)-NH2 |
| 3197 | Cys*-Phe-Trp-(D)Trp-Lys-Thr-Phe-Gly(S2)-NH2 |
| 3189 | H-Ala(C3)-Phe-(D)Trp-Lys-Phe-Ala(C3)-Thr-NH2; bridge-piperazine |
| 3191 | H-Ala(C3)-Phe-(D)Trp-Lys-Phe-Ala(C3)-Thr-NH2 bridge-1,2 diaminocyclohexane |
| 3193 | H-Ala(C3)-Phe-(D)Trp-Lys-Phe-Ala(C3)-Thr-NH2 bridge-m-xylenediamine |
| 3195 | H-Ala(C3)-Phe-(D)Trp-Lys-Phe-Ala(C3)-Thr-NH2 bridge-ethylene diamine |

The asterisk designates that the bridging group is connected between the $N^\alpha$-ω-functionalized derivative of an amino acid and the side chain of the marked residue.

For the last 4 analogs (PTR 3189, 3191, 3193, and 3195), two identical building units are connected by the different diamine bridges as indicated.

TABLE 14

Additional somatostatin analogs. Position in SRIF sequence

| PTR | 5 | 6 | 7 | 8 | 9 | 10 | 11 | 12 |
|---|---|---|---|---|---|---|---|---|
| 3905 | | Phe* | Phe | (D)Trp | Lys | Thr | Phe(C2) | |
| 3910 | | | Phe* | (D)Trp | Lys | Thr | Phe(C2) | |
| 3915 | | | Phe* | (D)Trp | (D)Lys | Thr | Phe(C2) | |
| 3920 | | | Ala(C1) | (D)Trp | Lys | Ala(N2) | Phe | |
| 3925 | | | Ala(C1) | (D)Trp | Lys | Thr | Phe(N2) | |
| 3930 | | | Ala(C1) | (D)Trp | Lys | Thr | Ala(N2) | |
| 3935 | | Ala(C1) | Phe | (D)Trp | Lys | Thr | Ala(N2) | |
| 3940 | | Ala(C1) | Tyr | (D)Trp | Lys | Val | Phe(N2) | |
| 3945 | | Ala* | Phe | (D)Trp | (D)Lys | Thr | Ala(N2) | |
| 3950 | (D)Phe | Ala(C1) | Phe | (D)Trp | Lys | Ala(N2) | | |
| 3955 | | | Ala* | (D)Trp | Lys | Thr | Ala(C2) | |
| 3960 | | | Ala(S2) | (D)Trp | Lys | Thr | Cys | |
| 3965 | | | Ala(S2) | (D)Trp | Lys | Thr | Cys | Thr-Ol |
| 3970 | | Ala(S2) | Phe | (D)Trp | Lys | Cys | | |
| 3975 | | Ala(S2) | Phe | (D)Trp | Lys | Thr | Cys | Thr-Ol | the asterisk denotes that the bridging group is connected between the $N^\alpha$-ω-functionalized derivative of an amino acid and the N terminus of the peptide. The Thr residues at position 12 in PTR 3965 and PTR 3975 are preferably reduced to a terminal alcohol group.

Example 12

Additional Preferred Backbone Cyclized Somatostatin Analogs Containing SH-building Units.

Additional preferred analogs which contain at list one SH-type building units are listed in table 12 with their binding affinities to SST-Rs. The asterisks in each PTR sequence designate the places of cyclization. The bridging group is connected between the marked $N^\alpha$-ω-S-functionalized derivative of an amino acid and another marked $N^\alpha$-ω-S-functionalized derivative of an amino acid, the side chain of Cys residue, or another SH-moiety.

TABLE 15

Additional preferred analogs containing SH-type building units.

| PTR | Sequence | IC$_{50}$ (nM) for SST-R | | | |
|---|---|---|---|---|---|
| 3159 | Fmoc-Gly(S1)-Phe-(D)Trp-Lys-Thr-Cys-Thr-OL | 1 | 2 | 3 | 5 |
| 3167 | (D)Phe-Gly(S1)-(D)Trp-Lys-Thr-Cys*-Thr-OL | | | | |
| 3169 | Gly(S1)-(D)Trp-Lys-Thr-Cys*-Thr-OL | | | | |
| 3175 | Phe(S4)-Tyr-(D)Trp-Lys-Val-Cys*-Thr-NH$_2$ | | | | |
| 3177 | Phe(S4)-Tyr-(D)Trp-Lys-Val-Cys*-Trp-NH$_2$ | | | | |
| 3179 | Fmoc-Gly(S1)-Tyr-(D)Trp-Lys-Val-Cys*-Thr-NH$_2$ | | | | |
| 3181 | Fmoc-Gly(S1)-Tyr-(D)Trp-Lys-Val-Cys*-Trp-NH$_2$ | | | | |
| 3197 | Cys*-Phe-Trp-(D)Trp-Lys-Thr-Phe-Gly(S2)*-NH$_2$ | 1000 | 4 | 40 | 1 |
| 3207 | (D)Phe-Cys*-Phe-Trp-(D)Trp-Lys-Thr-Phe-Gly(S2)*-NH$_2$ | <333 | 1–12 | | 4 |
| 3211 | Mercapto-acetic-acid(*)-Phe-Trp-(D)Trp-Lys-Thr-Phe-Gly(S2)*-NH$_2$ | 333 | 37 | 12–37 | 1.3 |
| 3213 | Gly(S2)*-Phe-Trp-(D)Trp-Lys-Thr-Phe-Gly(S2)*-NH$_2$ | 333 | 4 | 333 | 12 |
| 3217 | 3-Thiopropanoic-acid*-Phe-Trp-(D)Trp-Lys-Thr-Phe-Gly(S2)*-NH$_2$ | >333 | 37 | 100 | 4.1 |
| 3219 | (D)Phe-Gly(S2)*-Phe-Trp-(D)Trp-Lys-Thr-Phe-Gly(S2)*-NH$_2$ | >333 | 4 | 333 | 37 |
| 3221 | (D)Nal-Gly(S2)*-Phe-Trp-(D)Trp-Lys-Thr-Phe-Gly(S2)*-NH$_2$ | >333 | 12 | 333 | 111 |

The present invention has been exemplified herein by means of certain non-limitative examples. It will be clear to the skilled artisan that many further modifications and variations to the preferred embodiments are possible, without departing from the scope of the invention, which is to be construed by the scope of the claims which follow.

---

SEQUENCE LISTING

```
<160> NUMBER OF SEQ ID NOS: 10

<210> SEQ ID NO 1
<211> LENGTH: 14
<212> TYPE: PRT
<213> ORGANISM: mammalian

<400> SEQUENCE: 1

Ala Gly Cys Lys Asn Phe Phe Trp Lys Thr Phe Thr Ser Cys
1               5                   10

<210> SEQ ID NO 2
<211> LENGTH: 6
<212> TYPE: PRT
<213> ORGANISM: Artificial sequence
<220> FEATURE:
<221> NAME/KEY: DISULFIDE BRIDGE
<222> LOCATION: (1)..(1)
<223> OTHER INFORMATION: Cys residues at amino acid positions 1 and 6
      form a disulfide bridge
<220> FEATURE:
<221> NAME/KEY: MOD_RES
<222> LOCATION: (3)..(3)
<223> OTHER INFORMATION: The Trp residue is the D isomer
<220> FEATURE:
<223> OTHER INFORMATION: Synthetic peptide

<400> SEQUENCE: 2

Cys Phe Trp Lys Thr Cys
1               5

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: N-Methyl
<220> FEATURE:
<221> NAME/KEY: MOD_RES
<222> LOCATION: (1)..(6)
<223> OTHER INFORMATION: cyclo
```

```
<220> FEATURE:
<221> NAME/KEY: MOD_RES
<222> LOCATION: (3)..(3)
<223> OTHER INFORMATION: The Trp residue is the D isomer
<220> FEATURE:
<223> OTHER INFORMATION: Synthetic peptide

<400> SEQUENCE: 3

Ala Tyr Trp Lys Val Phe
1               5

<210> SEQ ID NO 4
<211> LENGTH: 8
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: The Phe residue is a D isomer
<220> FEATURE:
<221> NAME/KEY: MOD_RES
<222> LOCATION: (8)..(8)
<223> OTHER INFORMATION: The Thr residue ends with CH2OH
<220> FEATURE:
<221> NAME/KEY: DISULFIDE BRIDGE
<222> LOCATION: (2)..(2)
<223> OTHER INFORMATION: A disulfide bridge is formed between Cys
      residues 2 and 7
<220> FEATURE:
<221> NAME/KEY: MOD_RES
<222> LOCATION: (4)..(4)
<223> OTHER INFORMATION: The Trp residue is a D isomer
<220> FEATURE:
<223> OTHER INFORMATION: Synthetic peptide

<400> SEQUENCE: 4

Phe Cys Phe Trp Lys Thr Cys Thr
1               5

<210> SEQ ID NO 5
<211> LENGTH: 7
<212> TYPE: PRT
<213> ORGANISM: Artificial Sequence
<220> FEATURE:
<221> NAME/KEY: DISULFIDE
<222> LOCATION: (2)..(2)
<223> OTHER INFORMATION: A Disulfide Bridge is formed between the Cys
      residues at position 2 and 6
<220> FEATURE:
<221> NAME/KEY: MOD_RES
<222> LOCATION: (1)..(1)
<223> OTHER INFORMATION: The Phe residue is a D isomer
<220> FEATURE:
<221> NAME/KEY: MOD_RES
<222> LOCATION: (4)..(4)
<223> OTHER INFORMATION: The Trp residue is a D isomer
<220> FEATURE:
<221> NAME/KEY: MOD_RES
<222> LOCATION: (7)..(7)
<223> OTHER INFORMATION: The Thr residue ends with N2H
<220> FEATURE:
<223> OTHER INFORMATION: Synthetic peptide

<400> SEQUENCE: 5

Phe Cys Phe Trp Lys Cys Thr
1               5

<210> SEQ ID NO 6
<211> LENGTH: 8
<212> TYPE: PRT
<213> ORGANISM: Artificial sequence
<220> FEATURE:
<221> NAME/KEY: MISC_FEATURE
```

```
<222> LOCATION: (1)..(1)
<223> OTHER INFORMATION: is a gamma amino butyric acid, diamino butyric
      acid, Gly, beta-Ala, 5-amino pentanoic acid or amino hexanoic
      acid; Residue 1 is bridged to Residue 8; Residue 1 also begins
      with a hydrogen, or a mono- or di- saccharide attached
<220> FEATURE:
<221> NAME/KEY: MISC_FEATURE
<222> LOCATION: (2)..(2)
<223> OTHER INFORMATION: is (D) or (L) Phe or Tyr
<220> FEATURE:
<221> NAME/KEY: MISC_FEATURE
<222> LOCATION: (3)..(3)
<223> OTHER INFORMATION: is (D) or (L)-Trp, or (L)-Phe, (D)- or
      (L)-1Nal or (D) or (L)-2Nal, or Tyr
<220> FEATURE:
<221> NAME/KEY: MISC_FEATURE
<222> LOCATION: (4)..(4)
<223> OTHER INFORMATION: is (D) or (L)-Trp
<220> FEATURE:
<221> NAME/KEY: MISC_FEATURE
<222> LOCATION: (5)..(5)
<223> OTHER INFORMATION: is (D) or (L)-Lys
<220> FEATURE:
<221> NAME/KEY: MISC_FEATURE
<222> LOCATION: (6)..(6)
<223> OTHER INFORMATION: is Thr, Gly, Abu, Ser, Cys, Val, (D) or
      (L)-Ala, or (D)- or (L)-Ala, or Tyr
<220> FEATURE:
<221> NAME/KEY: MISC_FEATURE
<222> LOCATION: (7)..(7)
<223> OTHER INFORMATION: is (D) or (L)-Phe, or (D)- or (L)-Ala, Nle, or
      Cys
<220> FEATURE:
<221> NAME/KEY: MISC_FEATURE
<222> LOCATION: (8)..(8)
<223> OTHER INFORMATION: is Gly, Val, Leu, (D) or (L)-Phe, or 1Nal or
      2Nal; with a terminal carboxy acid, amide or alcohol group
<220> FEATURE:
<223> OTHER INFORMATION: Synthetic peptide

<400> SEQUENCE: 6

Xaa Xaa Xaa Xaa Xaa Xaa Xaa Xaa
1               5

<210> SEQ ID NO 7
<211> LENGTH: 7
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: is (D)- or (L)-Phe, or (D)- or (L)-Ala; wherein
      Residue 1 is bridged to Residue 6 a bridging group composed of
      1 to 5 methyl spacers connected to an amide, thioether, thioester,
      or disulfide, followed by 1 to 5 methyl spacers
<220> FEATURE:
<221> NAME/KEY: MISC_FEATURE
<222> LOCATION: (2)..(2)
<223> OTHER INFORMATION: is Tyr or (D)- or (L)-Phe
<220> FEATURE:
<221> NAME/KEY: MISC_FEATURE
<222> LOCATION: (3)..(3)
<223> OTHER INFORMATION: is (D)- or (L)-Trp, (D)- or (L)-1Nal, or
      (D)- or (L)-2Nal
<220> FEATURE:
<221> NAME/KEY: MISC_FEATURE
<222> LOCATION: (5)..(5)
<223> OTHER INFORMATION: is Thr, Val, Ser, or Cys
<220> FEATURE:
<221> NAME/KEY: MISC_FEATURE
<222> LOCATION: (6)..(6)
<223> OTHER INFORMATION: is Gly or  (D)- or (L)-Phe
<220> FEATURE:
<221> NAME/KEY: MISC_FEATURE
<222> LOCATION: (7)..(7)
<223> OTHER INFORMATION: is Thr, GABA, (D)- or (L)-1Nal, (D)- or
      (L)-2Nal, or (D)- or (L)-Phe
```

```
<220> FEATURE:
<223> OTHER INFORMATION: Synthetic peptide

<400> SEQUENCE: 7

Xaa Xaa Xaa Lys Xaa Xaa Xaa
1               5

<210> SEQ ID NO 8
<211> LENGTH: 12
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: is absent or is any amino acid
<220> FEATURE:
<221> NAME/KEY: MISC_FEATURE
<222> LOCATION: (2)..(2)
<223> OTHER INFORMATION: is absent or is any amino acid
<220> FEATURE:
<221> NAME/KEY: MISC_FEATURE
<222> LOCATION: (3)..(3)
<223> OTHER INFORMATION: is absent or is any amino acid
<220> FEATURE:
<221> NAME/KEY: MISC_FEATURE
<222> LOCATION: (4)..(4)
<223> OTHER INFORMATION: is absent or is any amino acid
<220> FEATURE:
<221> NAME/KEY: MISC_FEATURE
<222> LOCATION: (5)..(5)
<223> OTHER INFORMATION: is 1Nal, 2Nal, Beta-Asp (Ind), Gly, Tyr,
      (D)- or (L)-Ala, or (D)- or (L)-Phe
<220> FEATURE:
<221> NAME/KEY: MISC_FEATURE
<222> LOCATION: (6)..(7)
<223> OTHER INFORMATION: may be absent, or are independently Gly, Tyr,
      1Nal, 2Nal, Beta-Asp (Ind), Gly, Tyr, (D)- or (L)-Ala, or (D)- or
      (L)-Phe
<220> FEATURE:
<221> NAME/KEY: MISC_FEATURE
<222> LOCATION: (8)..(8)
<223> OTHER INFORMATION: (D)- or (L)-Trp
<220> FEATURE:
<221> NAME/KEY: MISC_FEATURE
<222> LOCATION: (9)..(9)
<223> OTHER INFORMATION: (D)- or (L)-Lys
<220> FEATURE:
<221> NAME/KEY: MISC_FEATURE
<222> LOCATION: (10)..(10)
<223> OTHER INFORMATION: is absent or is Gly, Abu, Cys, Thr, Val,
      (D)- or (L)-Ala, or (D)- or (L)-Phe
<220> FEATURE:
<221> NAME/KEY: MISC_FEATURE
<222> LOCATION: (11)..(11)
<223> OTHER INFORMATION: is Cys, (D)- or (L)-Ala, or  (D)- or (L)-Phe
<220> FEATURE:
<221> NAME/KEY: MISC_FEATURE
<222> LOCATION: (12)..(12)
<223> OTHER INFORMATION: is absent or is Val, Thr, 1Nal or 2Nal
<220> FEATURE:
<223> OTHER INFORMATION: Synthetic peptide

<400> SEQUENCE: 8

Xaa Xaa Xaa Xaa Xaa Xaa Xaa Xaa Xaa Xaa Xaa Xaa
1               5                   10

<210> SEQ ID NO 9
<211> LENGTH: 7
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: (D)- or (L)-Phe, Tyr or (D)- or (L)-Ala;
      Residue 1 is connected to Residue 7 by a bridge comprised of 1 to
```

```
      5 methylene spacers conncected to an amide, thioether, thioester,
      or disulfide, followed by 1 to 5 methylene spacers
<220> FEATURE:
<221> NAME/KEY: MISC_FEATURE
<222> LOCATION: (2)..(2)
<223> OTHER INFORMATION: (D)- or (L)-Phe, Tyr or (D)- or (L)-Ala;
<220> FEATURE:
<221> NAME/KEY: MISC_FEATURE
<222> LOCATION: (3)..(3)
<223> OTHER INFORMATION: is absent or is (D)- or (L)-Phe, Tyr or (D)- or
      (L)-Ala
<220> FEATURE:
<221> NAME/KEY: MISC_FEATURE
<222> LOCATION: (4)..(4)
<223> OTHER INFORMATION: is (D)- or (L)Tyr
<220> FEATURE:
<221> NAME/KEY: MISC_FEATURE
<222> LOCATION: (5)..(5)
<223> OTHER INFORMATION: is (D)- or (L)-Lys
<220> FEATURE:
<221> NAME/KEY: MISC_FEATURE
<222> LOCATION: (6)..(6)
<223> OTHER INFORMATION: is absent or is Thr, Val, Cys or (D)- or
      (L)-Ala
<220> FEATURE:
<221> NAME/KEY: MISC_FEATURE
<222> LOCATION: (7)..(7)
<223> OTHER INFORMATION: is a (D)- or (L)-Phe, Cys, or (D)- or (L)-Ala
<220> FEATURE:
<223> OTHER INFORMATION: Synthetic peptide

<400> SEQUENCE: 9

Xaa Xaa Xaa Xaa Xaa Xaa Xaa
1               5

<210> SEQ ID NO 10
<211> LENGTH: 7
<212> TYPE: PRT
<213> ORGANISM: Artificial Sequence
<220> FEATURE:
<221> NAME/KEY: MISC_FEATURE
<222> LOCATION: (1)..(1)
<223> OTHER INFORMATION: is absent or is (D)- or (L)-Phe or Ala; the
      bridge is connected to Residue 1 or 2 and Residue 6 or 7, wherein
      the bridge is comprised of 1 to 5 methylene spacers connected to
      an amide, thioether, thioester, or disulfide, followed by 1 to 5
      methylene
<220> FEATURE:
<223> OTHER INFORMATION: spacers
<220> FEATURE:
<221> NAME/KEY: MISC_FEATURE
<222> LOCATION: (2)..(2)
<223> OTHER INFORMATION: is (D)- or (L)-Phe or Ala, Tyr
<220> FEATURE:
<221> NAME/KEY: MISC_FEATURE
<222> LOCATION: (3)..(3)
<223> OTHER INFORMATION: is (D)- or (L)-Trp
<220> FEATURE:
<221> NAME/KEY: MISC_FEATURE
<222> LOCATION: (4)..(4)
<223> OTHER INFORMATION: is (D)- or (L)-Lys
<220> FEATURE:
<221> NAME/KEY: MISC_FEATURE
<222> LOCATION: (5)..(5)
<223> OTHER INFORMATION: is Thr, Ala, Val, or Cys
<220> FEATURE:
<221> NAME/KEY: MISC_FEATURE
<222> LOCATION: (6)..(6)
<223> OTHER INFORMATION: is absent or is (D)- or (L)-Phe, Ala, or Cys
<220> FEATURE:
<221> NAME/KEY: MISC_FEATURE
<222> LOCATION: (7)..(7)
```

```
<223> OTHER INFORMATION: is absent or is Thr or Thr reduced to an
      alcohol
<220> FEATURE:
<223> OTHER INFORMATION: Synthetic peptide

<400> SEQUENCE: 10

Xaa Xaa Xaa Xaa Xaa Xaa Xaa
1               5
```

What is claimed is:

1. A backbone cyclized somatostatin analog comprising a peptide sequence of four to twelve amino acids that incorporates at least one building unit, said building unit containing one nitrogen atom of the peptide backbone connected to a bridging group comprising an amide, thioether, thioester, or disulfide, wherein the at least one building unit is connected via the bridging group to form a cyclic structure with a moiety selected from the group consisting of a second building unit, the side chain of an amino acid residue of the sequence or the N-terminal amino acid residue, wherein the sequence includes a non-cyclized chain of 4, 5 or 6 amino acids.

2. The backbone cyclized somatostatin analog of claim 1 having the general formula 7:

Formula No.7

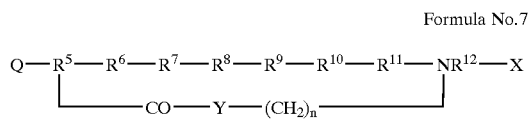

(SEQ ID NO: 6)

wherein n is 1 to 5;

X designates a terminal carboxy acid, amide or alcohol group;

Q is hydrogen or a mono- or di-saccharide $R^5$ is gamma amino butyric acid, diamino butyric acid, Gly, α-Ala, 5-amino pentanoic acid or amino hexanoic acid;

$R^6$ is (D)- or (L)-Phe or Tyr;

$R^7$ is (D)- or (L)-Trp, (D)- or (L)-Phe, (D)- or (L)-1Nal, (D)- or (L)-2Nal, or Tyr;

$R^8$ is (D)- or (L)-Trp;

$R^9$ is (D)- or (L)-Lys;

$R^{10}$ is Thr, Gly, Abu, Ser, Cys, Val, (D)- or (L)-Ala, or (D)- or (L)-Phe;

$R^{11}$ is (D)- or (L)-Phe, (D)- or (L)-Ala, Nle, or Cys;

$R^{12}$ is Gly, Val, Leu, (D)- or (L)-Phe, 1Nal, or 2Nal; and

Y is amide, thioether, thioester or disulfide.

3. The backbone cyclized somatostatin analog of claim 2 wherein:

Q is hydrogen;

$R^5$ is GABA;

$R^6$ is Phe;

$R^7$ is Trp;

$R^8$ is (D)-Trp;

$R^9$ is Lys;

$R^{10}$ is Thr;

$R^{11}$ is Phe;

$R^{12}$ is Gly;

n is 3; and

Y is an amide.

4. The backbone cyclized somatostatin analog of claim 2 wherein:

Q is galactose;

$R^5$ is Dab;

$R^6$ is Phe;

$R^7$ is (L)-Trp;

$R^8$ is (D)-Trp;

$R^9$ is Lys;

$R^{10}$ is Thr;

$R^{11}$ is Phe;

$R^{12}$ is Gly;

n is 3; and

Y is an amide.

5. The backbone cyclized somatostatin analog of claim 1 having the general formula 8:

Formula No.8

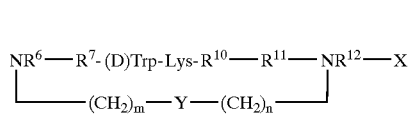

wherein:

m and n are 1 to 5;

X designates a terminal carboxy acid, amide or alcohol group;

$R^6$ is (D)- or (L)-Phe, or (D)- or (L)-Ala;

$R^7$ is Tyr, (D)- or (L)-Ala, or (D)- or (L)-Phe;

$R^{10}$ is Thr, Val, Ser, or Cys;

$R^{11}$ is Val, (D)- or (L)-1Nal, (D)- or (L)-2Nal, or (D) or (L)-Phe;

$R^{12}$ is Gly, (D)- or (L)-Ala, or (D) or (L)-Phe; and

Y is amide, thioether, thioester or disulfide.

6. The backbone cyclized somatostatin analog of claim 5 wherein:

$R^6$ is (D)- or (L)-Phe;

$R^7$ is Tyr or Phe;

$R_{10}$ is Thr, Val or Ser;

$R^{11}$ is Val, 1Nal, or 2Nal;

$R^{12}$ is Gly; and

Y is amide.

7. The backbone cyclized somatostatin analog of claim 1 having the general formula 9:

Formula No.9

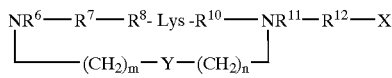

(SEQ ID NO: 7)

wherein:
m and n are 1 to 5;
X designates a terminal carboxy acid, amide or alcohol group;
$R^6$ is (D)- or (L)-Phe, or (D)- or (L)-Ala;
$R^7$ is Tyr or (D)- or (L)-Phe;
$R^8$ is (D)- or (L)-Trp, (D)- or (L)-1Nal, or (D)- or (L)-2Nal;
$R^{10}$ is Thr, Val, Ser, or Cys;
$R^{11}$ is Gly or (D) or (L)-Phe;
$R^{12}$ is Thr, GABA, (D)- or (L)-1Nal, (D)- or (L)-2Nal, or (D) or (L)-Phe; and
Y is amide, thioether, thioester or disulfide.

8. The backbone cyclized somatostatin analog of claim 7 wherein:
$R^6$ is (D)- or (L)-Phe;
$R^7$ is Tyr;
$R^8$ is (D)Trp, (D)1Nal, or (D)2Nal;
$R^{10}$ is Val;
$R^{11}$ is Gly;
$R^{12}$ is Thr, 1Nal, or 2Nal; and
Y is amide.

9. The backbone cyclized somatostatin analog of claim 1 having the general formula 13:

Formula No.13

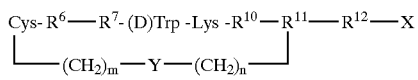

wherein m and n are 1 to 5;
X designates a terminal carboxy acid, amide or alcohol group;
$R^6$ is (D)- or (L)-Phe or Tyr;
$R^7$ is (D)- or (L)-Trp, (D)- or (L)-Phe, (D)- or (L)-1Nal or (D)- or (L)-2Nal, or Tyr;
$R^{10}$ is Thr, Gly, Abu, Ser, Cys, Val, (D)- or (L)-Ala, or (D)- or (L)-Phe;
$R^{11}$ is (D)- or (L)-Phe or (D)- or (L)-Ala;
$R^{12}$ is Gly, Val, or (D)- or (L)-Phe; and
Y is thioether, thioester or disulfide.

10. The backbone cyclized somatostatin analog of claim 9 wherein:
$R^6$ is Phe;
$R^7$ is Trp;
$R^{10}$ is Thr;
$R^{11}$ is Phe;
$R^{12}$ is Gly; and
Y is disulfide.

11. The backbone cyclized somatostatin analog of claim 1 having the general formula 14:

Formula No. 14

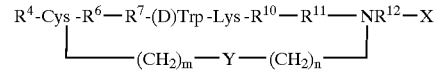

wherein
m and n are 1 to 5;
X designates a terminal carboxy acid, amide or alcohol group;
$R^4$ is (D)- or (L)-Phe or Tyr;
$R^6$ is (D)- or (L)-Phe or Tyr;
$R^7$ is (D)- or (L)-Trp, (D)- or (L)-Phe, (D)- or (L)-1Nal or (D)- or (L)-2Nal, or Tyr;
$R^{10}$ is Thr, Gly, Abu, Ser, Cys, Val, (D)- or (L)-Ala, or (D)- or (L)-Phe;
$R^{11}$ is (D)- or (L)-Phe or (D)- or (L)-Ala;
$R^{12}$ is Gly, Val, or (D)- or (L)-Phe; and
Y is thioether, thioester or disulfide.

12. The backbone cyclized somatostatin analog of claim 11 wherein:
$R^4$ is (D)Phe;
$R^6$ is Phe;
$R^7$ is Trp;
$R^{10}$ is Thr;
$R^{11}$ is Phe;
$R^{12}$ is Gly; and
Y is disulfide.

13. The backbone cyclized somatostatin analog of claim 1 having the general formula 15:

Formula No. 5

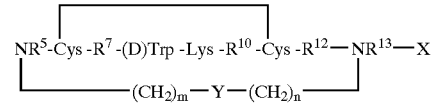

wherein
m and n are 1 to 5;
X designates a terminal carboxy acid, amide or alcohol group;
$R^5$ is (D)- or (L)-Phe or (D)- or (L)-Ala;
$R^7$ is (D)- or (L)-Trp, (D)- or (L)-Phe, (D)- or (L)-1Nal or (D)- or (L)-2Nal, or Tyr;
$R^{10}$ is Thr, Gly, Abu, Ser, Cys, Val, (D)- or (L)-Ala, or (D)- or (L)-Phe;
$R^{12}$ is Gly, Val, or (D)- or (L)-Phe, or is absent;
$R^{13}$ is (D)- or (L)-Phe or (D)- or (L)-Ala; and
Y is amide, thioether, thioester or disulfide.

14. The backbone cyclized somatostatin analog of claim 13 wherein:
$R^5$ is Phe;
$R^7$ is Phe;
$R^{10}$ is Thr;
$R^{12}$ is Gly, Val, or (D)- or (L)-Phe, or is absent;
$R^{13}$ is Phe; and
Y is amide.

15. The backbone cyclized somatostatin analog of claim 1 having the formula:
Phe(N2)-Tyr-(D)2Nal-Lys-Val-Gly(C2)-Thr-X;
Phe(N2)-Tyr-(D)Trp-Lys-Val-Gly(C2)-2Nal-X;

Phe(N2)-Tyr-(D)Trp-Lys-Val-Val-Gly(C2)-X;

Phe(N2)-Tyr-(D)Trp-Lys-Ser-2Nal-Gly(C2)-X;

Phe(N2)-Phe-(D)Trp-Lys-Thr-2Nal-Gly(C2)-X;

GABA*-Phe-Trp-(D)Trp-Lys-Thr-Phe-Gly(C3)-X;

Cys*-Phe-Trp-(D)Trp-Lys-Thr-Phe-Gly(S2)-X;

Phe(C3)-Cys*-Phe-(D)Trp-Lys-Thr-Cys*-Phe-Phe(N3)-X;

(D)Phe-Cys*-Phe-Trp-(D)Trp-Lys-Thr-Phe-Gly(S2)-X; or

Galactose-Dab*-Phe-Trp-(D)Trp-Lys-Thr-Phe-Gly(C3)-X;

wherein X designates a terminal carboxy acid, amide, or alcohol group; the asterisk denotes that the bridging group is connected between the $N^{\alpha}$-$\omega$-functionalized derivative of an amino acid and the N-terminus of the peptide or the side chain of the Cys residue.

16. A pharmaceutical composition comprising a backbone cyclized somatostatin analog according to claim 1 and a pharmaceutically acceptable carrier.

17. The composition according to claim 16 wherein the backbone cyclic analog is selective for one somatostatin receptor subtypes.

18. The composition according to claim 16 wherein the backbone cyclic analog is selective for two somatostatin receptor subtypes.

* * * * *

UNITED STATES PATENT AND TRADEMARK OFFICE
CERTIFICATE OF CORRECTION

| | |
|---|---|
| PATENT NO. | : 6,930,088 B2 |
| APPLICATION NO. | : 09/734583 |
| DATED | : August 16, 2005 |
| INVENTOR(S) | : Hornik et al. |

It is certified that error appears in the above-identified patent and that said Letters Patent is hereby corrected as shown below:

<u>Title Page</u>:
Item (73) Assignee, change "Peptor Ltd." to -- DeveloGen Israel Ltd. --.
Item (56) References Cited, OTHER PUBLICATIONS:
Hruby et al. reference, after "Biochem. J." change "298" to -- 268 --.

Signed and Sealed this

Twenty-fifth Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 6,930,088 B2
APPLICATION NO. : 09/734583
DATED : August 16, 2005
INVENTOR(S) : Hornik et al.

Page 1 of 1

It is certified that error appears in the above-identified patent and that said Letters Patent is hereby corrected as shown below:

In the Specification

Column 17:
Lines 5-7, replace Formula No. 13 with the following:

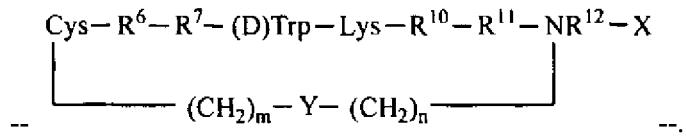

--.

Lines 37-39, replace Formula No. 14 with the following:

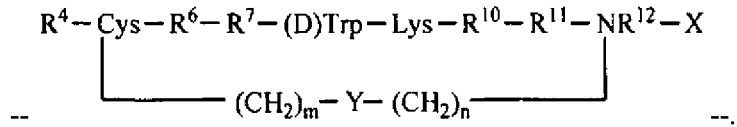

--.

In the Claims

Column 49:
Lines 40-42, replace Formula No. 13 with the following:

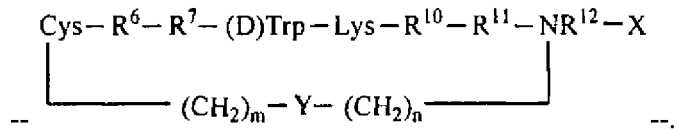

--.

Signed and Sealed this
Twenty-ninth Day of September, 2015

Michelle K. Lee
*Director of the United States Patent and Trademark Office*